(12) United States Patent
Schneider

(10) Patent No.: US 12,108,225 B2
(45) Date of Patent: *Oct. 1, 2024

(54) IMPLANTABLE DEVICE FOR SUSTAINED RELEASE OF A MACROMOLECULAR DRUG COMPOUND

(71) Applicant: Celanese EVA Performance Polymers LLC, Irving, TX (US)

(72) Inventor: Christian Schneider, Hattersheim am Main (DE)

(73) Assignee: Celanese EVA Performance Polymers LLC, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/315,618

(22) Filed: May 11, 2023

(65) Prior Publication Data

US 2023/0277469 A1 Sep. 7, 2023

Related U.S. Application Data

(63) Continuation of application No. 16/416,328, filed on May 20, 2019, now Pat. No. 11,690,806.

(60) Provisional application No. 62/675,995, filed on May 24, 2018.

(51) Int. Cl.
| | |
|---|---|
| A61K 9/50 | (2006.01) |
| A61K 38/39 | (2006.01) |
| A61K 38/47 | (2006.01) |
| A61K 49/04 | (2006.01) |
| G10L 21/0232 | (2013.01) |
| G10L 21/028 | (2013.01) |
| H04R 3/00 | (2006.01) |
| H04R 3/04 | (2006.01) |
| H04R 5/04 | (2006.01) |
| G10L 21/0216 | (2013.01) |

(52) U.S. Cl.
CPC .......... *H04R 3/005* (2013.01); *A61K 9/5026* (2013.01); *A61K 9/5031* (2013.01); *A61K 9/5073* (2013.01); *A61K 9/5089* (2013.01); *A61K 38/39* (2013.01); *A61K 38/47* (2013.01); *A61K 49/04* (2013.01); *C12Y 304/22032* (2013.01); *C12Y 304/22033* (2013.01); *G10L 21/0232* (2013.01); *G10L 21/028* (2013.01); *H04R 3/04* (2013.01); *H04R 5/04* (2013.01); *G10L 2021/02166* (2013.01)

(58) Field of Classification Search
CPC ..... A61K 9/0024; A61K 31/496; A61K 31/65
See application file for complete search history.

(56) References Cited

U.S. PATENT DOCUMENTS

| | | | |
|---|---|---|---|
| 4,014,335 A | 3/1977 | Arnold | |
| 4,069,307 A | 1/1978 | Higuchi et al. | |
| 4,164,560 A | 8/1979 | Folkman et al. | |
| 4,357,312 A | 11/1982 | Hsieh et al. | |
| 4,391,797 A | 7/1983 | Folkman et al. | |
| 4,663,147 A | 5/1987 | DePrince | |
| 4,666,704 A | 5/1987 | Shalati et al. | |
| 4,792,448 A | 12/1988 | Ranade | |
| 4,863,735 A | 9/1989 | Kohn et al. | |
| 4,883,666 A | 11/1989 | Sabel et al. | |
| 4,891,225 A | 1/1990 | Langer et al. | |
| 4,898,734 A | 2/1990 | Mathiowitz et al. | |
| 4,900,556 A | 3/1990 | Wheatley et al. | |
| 4,933,185 A | 6/1990 | Wheatley et al. | |
| 4,952,406 A | 8/1990 | Brown et al. | |
| 4,957,119 A | 9/1990 | De Nijs | |
| 4,989,734 A | 2/1991 | Mode et al. | |
| 5,008,112 A | 4/1991 | DePrince et al. | |
| 5,088,505 A | 2/1992 | De Nijs | |
| 5,100,668 A | 3/1992 | Edelman et al. | |
| 5,150,718 A | 9/1992 | De Nijs | |
| 5,302,397 A | 4/1994 | Amsden et al. | |
| 5,324,523 A | 6/1994 | Zsuga et al. | |

(Continued)

FOREIGN PATENT DOCUMENTS

| | | |
|---|---|---|
| AU | 765149 B2 | 9/2003 |
| CA | 2176145 | 5/1995 |

(Continued)

OTHER PUBLICATIONS

Abstract—Almeida et al., "Ethylene vinyl acetate as matrix for oral sustained release dosage forms produced via hot-melt extrusion," *European Journal of Pharmaceutics and Biopharmaceutics*, vol. 77, Issue 2, Feb. 2011, pp. 297-305.

Abstract of Almeida, A. et al., "Sustained release from hot-melt extruded matrices based on ethylene vinyl acetate and polyethylene oxide," *European Journal of Pharmaceutics and Biopharmaceutics*, vol. 82, Issue 3, Nov. 2012, pp. 526-533.

Agarwal et al., "Injectable implants for the sustained release of protein and peptide drugs," *Drug Discovery Today*, vol. 18, Nos. 7/8, Apr. 2013, pp. 337-349.

(Continued)

*Primary Examiner* — Micah Paul Young
(74) *Attorney, Agent, or Firm* — Dority & Manning, P.A.

(57) ABSTRACT

An implantable device for delivery of a macromolecular drug compound is provided. The device comprises a core having an outer surface and a membrane layer positioned adjacent to the outer surface of the core. The core comprises a core polymer matrix within which is dispersed a drug compound having a molecular weight of about 0.5 kDa or more, the polymer matrix containing a hydrophobic polymer. Further, the membrane layer comprises a membrane polymer matrix within which the macromolecular drug compound is optionally dispersed. The membrane polymer matrix contains a hydrophobic polymer in combination with a hydrophilic compound, and the weight ratio of the hydrophobic polymer to the hydrophilic compound within the membrane polymer matrix ranges from about 0.25 to about 200.

21 Claims, 17 Drawing Sheets

(56) References Cited

U.S. PATENT DOCUMENTS

| | | |
|---|---|---|
| 5,330,768 A | 7/1994 | Park et al. |
| 5,378,475 A | 1/1995 | Smith et al. |
| 5,439,688 A | 8/1995 | Orsolini et al. |
| 5,512,293 A | 4/1996 | Landrau et al. |
| 5,514,378 A | 5/1996 | Mikos et al. |
| 5,543,465 A | 8/1996 | Bell et al. |
| 5,545,409 A | 8/1996 | Laurencin et al. |
| 5,601,835 A | 2/1997 | Sabel et al. |
| 5,626,862 A | 5/1997 | Brem et al. |
| 5,626,877 A | 5/1997 | Amsden et al. |
| 5,639,810 A | 6/1997 | Smith, III |
| 5,686,877 A | 11/1997 | Keller et al. |
| 5,733,565 A | 3/1998 | Moo-Young et al. |
| 5,783,567 A | 7/1998 | Hedley et al. |
| 5,827,525 A | 10/1998 | Liao et al. |
| 5,858,388 A | 1/1999 | Grossman et al. |
| 5,877,224 A | 3/1999 | Brocchini et al. |
| 5,902,598 A | 5/1999 | Chen et al. |
| 5,916,584 A | 6/1999 | O'Donoghue et al. |
| 5,989,581 A | 11/1999 | Groenewegen |
| 6,001,386 A | 12/1999 | Ashton et al. |
| 6,083,534 A | 7/2000 | Wallach et al. |
| 6,096,764 A | 8/2000 | Bryant et al. |
| 6,117,441 A | 9/2000 | Moo-Young et al. |
| 6,159,143 A | 12/2000 | Lennox |
| 6,217,895 B1 | 4/2001 | Guo et al. |
| 6,248,057 B1 | 6/2001 | Mavity et al. |
| 6,262,034 B1 | 7/2001 | Mathiowitz et al. |
| 6,281,015 B1 | 8/2001 | Mooney et al. |
| RE37,410 E | 10/2001 | Brem et al. |
| 6,331,313 B1 | 12/2001 | Wong et al. |
| 6,344,035 B1 | 2/2002 | Chudzik et al. |
| 6,375,972 B1 | 4/2002 | Guo et al. |
| 6,423,345 B2 | 7/2002 | Bernstein et al. |
| 6,459,917 B1 | 10/2002 | Gowda |
| 6,471,993 B1 | 10/2002 | Shastri et al. |
| 6,565,845 B2 | 5/2003 | Cherksey et al. |
| 6,565,874 B1 | 5/2003 | Dunn et al. |
| 6,544,546 B1 | 7/2003 | Joseph Groenewegen et al. |
| 6,689,390 B2 | 2/2004 | Bernstein et al. |
| 6,713,081 B2 | 3/2004 | Robinson et al. |
| 6,719,750 B2 | 4/2004 | Varner et al. |
| 6,730,322 B1 | 5/2004 | Bernstein et al. |
| 6,767,550 B1 | 7/2004 | Génin et al. |
| 6,918,927 B2 | 7/2005 | Bates et al. |
| 6,964,781 B2 | 11/2005 | Brubaker |
| 6,991,808 B2 | 1/2006 | Brubaker et al. |
| 7,005,454 B2 | 2/2006 | Brocchini et al. |
| 7,052,719 B2 | 5/2006 | Bernstein et al. |
| 7,097,850 B2 | 8/2006 | Chappa et al. |
| 7,115,256 B1 | 10/2006 | Allen et al. |
| 7,189,461 B2 | 3/2007 | Rabasco et al. |
| 7,195,774 B2 | 3/2007 | Carvalho et al. |
| 7,309,689 B2 | 12/2007 | Trigg et al. |
| 7,442,402 B2 | 10/2008 | Chudzik et al. |
| 7,452,866 B2 | 11/2008 | Thorn et al. |
| 7,531,503 B2 | 5/2009 | Atala et al. |
| 7,534,449 B2 | 5/2009 | Saltzman et al. |
| 7,594,899 B2 | 9/2009 | Pinchuk et al. |
| 7,666,445 B2 | 2/2010 | Siegel et al. |
| 7,708,711 B2 | 5/2010 | Tu et al. |
| 7,736,665 B2 | 6/2010 | Patel et al. |
| 7,763,277 B1 | 7/2010 | Canham et al. |
| 7,803,178 B2 | 9/2010 | Whirley et al. |
| 7,829,112 B2 | 11/2010 | Ron et al. |
| 7,833,168 B2 | 11/2010 | Taylor et al. |
| 7,833,545 B2 | 11/2010 | Ron et al. |
| 7,833,548 B2 | 11/2010 | Chappa et al. |
| 7,838,024 B2 | 11/2010 | Ron et al. |
| 7,871,643 B2 | 1/2011 | Lizio et al. |
| 7,883,718 B2 | 2/2011 | Ron et al. |
| 7,901,707 B2 | 3/2011 | Allen et al. |
| 7,989,018 B2 | 8/2011 | McNiven et al. |
| 8,021,680 B2 | 9/2011 | Anderson et al. |
| 8,039,010 B2 | 10/2011 | Trogden et al. |
| 8,096,972 B2 | 1/2012 | Varner et al. |
| 8,097,236 B2 | 1/2012 | Aston et al. |
| 8,119,154 B2 | 2/2012 | Huang et al. |
| 8,147,865 B2 | 4/2012 | Huang et al. |
| 8,173,163 B2 | 5/2012 | Kohn et al. |
| 8,182,464 B2 | 5/2012 | Lee et al. |
| 8,197,839 B2 | 6/2012 | Martinod et al. |
| 8,221,778 B2 | 7/2012 | Siegel et al. |
| 8,232,313 B2 | 7/2012 | Munn et al. |
| 8,236,857 B2 | 8/2012 | Dill |
| 8,257,730 B2 | 9/2012 | Huang et al. |
| 8,263,108 B2 | 9/2012 | Gibson et al. |
| 8,263,110 B2 | 9/2012 | Huang et al. |
| 8,273,375 B2 | 9/2012 | Lizio et al. |
| 8,298,565 B2 | 10/2012 | Taylor et al. |
| 8,298,570 B2 | 10/2012 | Huang et al. |
| 8,333,983 B2 | 12/2012 | Groenewegen et al. |
| 8,348,877 B2 | 1/2013 | Tu et al. |
| 8,399,518 B2 | 3/2013 | Morkin et al. |
| 8,440,216 B2 | 5/2013 | Huang et al. |
| 8,454,582 B2 | 6/2013 | deJuan et al. |
| 8,465,769 B2 | 6/2013 | Petereit et al. |
| 8,475,820 B2 | 7/2013 | Kuzma et al. |
| 8,481,079 B2 | 7/2013 | De Graaff et al. |
| 8,541,028 B2 | 9/2013 | Staas et al. |
| 8,568,766 B2 | 10/2013 | Anantharamaiah et al. |
| 8,568,778 B2 | 10/2013 | Lizio et al. |
| 8,580,735 B2 | 11/2013 | Francois et al. |
| 8,642,089 B2 | 2/2014 | Petereit et al. |
| 8,647,657 B2 | 2/2014 | Gibson et al. |
| 8,685,427 B2 | 4/2014 | Li et al. |
| 8,697,104 B2 | 4/2014 | Knezevich et al. |
| 8,722,037 B2 | 5/2014 | Veenstra et al. |
| 8,734,849 B2 | 5/2014 | Lizio et al. |
| 8,741,329 B2 | 6/2014 | de Graaff et al. |
| 8,747,883 B2 | 6/2014 | Labib et al. |
| 8,753,667 B2 | 6/2014 | Variano et al. |
| 8,765,152 B2 | 7/2014 | Lizio et al. |
| 8,765,166 B2 | 7/2014 | Kopezynski et al. |
| 8,771,722 B2 | 7/2014 | Huang et al. |
| 8,795,242 B2 | 8/2014 | Hoganson et al. |
| 8,795,707 B2 | 8/2014 | Wolinsky et al. |
| 8,808,744 B2 | 8/2014 | de Graaff et al. |
| 8,840,920 B2 | 9/2014 | Nugara et al. |
| 8,852,623 B2 | 10/2014 | Patel et al. |
| 8,858,977 B2 | 10/2014 | Groenewegen et al. |
| 8,858,993 B2 | 10/2014 | Gold et al. |
| 8,871,241 B2 | 10/2014 | Chou et al. |
| 8,889,174 B1 | 11/2014 | Gibson et al. |
| 8,900,615 B2 | 12/2014 | Groenewegen et al. |
| 8,900,616 B2 | 12/2014 | Belcheva et al. |
| 8,911,426 B2 | 12/2014 | Coppeta et al. |
| 8,911,427 B2 | 12/2014 | Seiler et al. |
| 8,962,009 B2 | 2/2015 | Huang et al. |
| 8,962,010 B2 | 2/2015 | Woolfson et al. |
| 8,962,011 B2 | 2/2015 | Raspagliesi |
| 8,980,298 B2 | 3/2015 | Schwarz |
| 8,992,979 B2 | 3/2015 | Emanuel et al. |
| 9,066,782 B2 | 6/2015 | Tu et al. |
| 9,078,900 B2 | 7/2015 | Kuzma et al. |
| 9,107,899 B2 | 8/2015 | Furst et al. |
| 9,132,081 B2 | 9/2015 | Loxley |
| 9,132,088 B2 | 9/2015 | Sim et al. |
| 9,175,162 B2 | 11/2015 | Pacetti et al. |
| 9,296,687 B2 | 3/2016 | George et al. |
| 9,301,926 B2 | 4/2016 | Indolfi et al. |
| 9,327,059 B2 | 5/2016 | Huang et al. |
| 9,345,686 B2 | 5/2016 | De Graaff |
| 9,370,444 B2 | 6/2016 | Cunningham, Jr. |
| 9,370,558 B2 | 6/2016 | Ali et al. |
| 9,492,400 B2 | 11/2016 | Jon et al. |
| 9,585,912 B2 | 3/2017 | Sherman et al. |
| 9,668,977 B2 | 6/2017 | Schattka et al. |
| 9,687,506 B2 | 6/2017 | Sherman et al. |
| 9,775,815 B2 | 10/2017 | Schattka et al. |
| 9,782,346 B2 | 10/2017 | Venkatraman et al. |
| 9,789,001 B2 | 10/2017 | Tu et al. |
| 9,808,420 B2 | 11/2017 | Kopczynski et al. |
| 9,814,671 B2 | 11/2017 | Lee |

(56) References Cited

U.S. PATENT DOCUMENTS

| | | |
|---|---|---|
| 9,821,045 B2 | 11/2017 | Ali et al. |
| 9,844,511 B2 | 12/2017 | Nollenberger et al. |
| 9,872,829 B2 | 1/2018 | Loxley et al. |
| 9,872,912 B2 | 1/2018 | Chiou et al. |
| 9,895,318 B2 | 2/2018 | Joshi et al. |
| 9,896,576 B2 | 2/2018 | Zhang et al. |
| 9,956,172 B2 | 5/2018 | McGinity et al. |
| 9,987,233 B2 | 6/2018 | Helliwell et al. |
| 9,999,595 B2 | 6/2018 | Rakic et al. |
| 10,010,612 B2 | 7/2018 | Dadey et al. |
| 10,028,851 B2 | 7/2018 | Dugan et al. |
| 10,029,034 B2 | 7/2018 | Falotico et al. |
| 10,058,554 B2 | 8/2018 | Luk et al. |
| 10,098,836 B2 | 10/2018 | Csaky |
| 10,111,830 B2 | 10/2018 | Patel et al. |
| 10,111,838 B2 | 10/2018 | Joshi et al. |
| 10,123,971 B2 | 11/2018 | Patel et al. |
| 10,226,419 B2 | 3/2019 | Arps et al. |
| 10,286,197 B2 | 5/2019 | Pouliot et al. |
| 10,413,504 B2 | 9/2019 | de Graaff et al. |
| 10,413,612 B2 | 9/2019 | Goldberg et al. |
| 10,434,063 B2 | 10/2019 | McGinity et al. |
| 10,435,469 B2 | 10/2019 | Goldberg et al. |
| 10,449,145 B2 | 10/2019 | Csaky |
| 10,548,766 B2 | 2/2020 | Cuevas |
| 10,568,949 B2 | 2/2020 | Ali et al. |
| 10,596,103 B2 | 3/2020 | Aarts et al. |
| 10,624,862 B2 | 4/2020 | Wening et al. |
| 10,639,283 B2 | 5/2020 | Haksar et al. |
| 10,653,621 B2 | 5/2020 | Wu et al. |
| 10,682,400 B2 | 6/2020 | Ali et al. |
| 10,702,551 B2 | 7/2020 | Stephan |
| 10,835,604 B2 | 11/2020 | Ngwa et al. |
| 10,836,826 B2 | 11/2020 | Goldberg et al. |
| 10,869,833 B2 | 12/2020 | Kopczynski et al. |
| 10,874,768 B2 | 12/2020 | Morgan et al. |
| 10,881,609 B2 | 1/2021 | Csaky |
| 11,021,539 B2 | 6/2021 | Goldberg et al. |
| 2002/0081556 A1 | 6/2002 | Tseng et al. |
| 2003/0149008 A1 | 8/2003 | Sahadevan |
| 2003/0203000 A1 | 10/2003 | Schwarz et al. |
| 2004/0121014 A1 | 6/2004 | Guo et al. |
| 2004/0224000 A1 | 11/2004 | Deghenghi |
| 2005/0031668 A1 | 2/2005 | Patel et al. |
| 2005/0220895 A1 | 10/2005 | Bucalo et al. |
| 2005/0244462 A1 | 11/2005 | Farooq |
| 2006/0003008 A1 | 1/2006 | Gibson et al. |
| 2006/0089410 A1 | 4/2006 | Bucalo et al. |
| 2006/0141049 A1 | 6/2006 | Lyons et al. |
| 2006/0147437 A1 | 7/2006 | Allen et al. |
| 2006/0160745 A1 | 7/2006 | Igari et al. |
| 2006/0188543 A1 | 8/2006 | Feng |
| 2007/0128294 A1 | 6/2007 | Bucalo et al. |
| 2007/0134332 A1 | 6/2007 | Turnell et al. |
| 2007/0179097 A1 | 8/2007 | Furuya et al. |
| 2007/0231406 A1 | 10/2007 | Bucalo et al. |
| 2007/0248637 A1 | 10/2007 | Chappa et al. |
| 2007/0260203 A1 | 11/2007 | Donello et al. |
| 2007/0275031 A1 | 11/2007 | Patel et al. |
| 2008/0145406 A1 | 6/2008 | Asgharian et al. |
| 2008/0166391 A1 | 7/2008 | Gibson et al. |
| 2009/0011007 A1 | 1/2009 | Meier et al. |
| 2009/0035381 A1 | 2/2009 | Stankus et al. |
| 2009/0092650 A1 | 4/2009 | Warren et al. |
| 2009/0104243 A1 | 4/2009 | Utkhede et al. |
| 2009/0117168 A1 | 5/2009 | Keenan |
| 2009/0130176 A1 | 5/2009 | Bossy-Nobs et al. |
| 2009/0142313 A1 | 6/2009 | Talling et al. |
| 2009/0173906 A1 | 7/2009 | Park et al. |
| 2009/0311304 A1 | 12/2009 | Borck et al. |
| 2010/0051575 A1 | 3/2010 | Ou |
| 2010/0104619 A1 | 4/2010 | De Graaff et al. |
| 2010/0158799 A1 | 6/2010 | Chudzik et al. |
| 2010/0158980 A1 | 6/2010 | Kopczynski et al. |
| 2010/0203104 A1 | 8/2010 | De Graaff et al. |
| 2010/0278725 A1 | 11/2010 | Liu et al. |
| 2010/0285097 A1 | 11/2010 | Talling et al. |
| 2010/0303883 A1 | 12/2010 | Pollock et al. |
| 2011/0038936 A1 | 2/2011 | Griswold et al. |
| 2011/0045076 A1 | 2/2011 | Kiser et al. |
| 2011/0105990 A1 | 5/2011 | Silvestrini |
| 2011/0230963 A1 | 9/2011 | Cuevas |
| 2011/0280922 A1 | 11/2011 | Ron et al. |
| 2012/0029042 A1 | 2/2012 | King |
| 2012/0078362 A1 | 3/2012 | Haffner et al. |
| 2012/0164193 A1 | 6/2012 | Dill |
| 2012/0207682 A1 | 8/2012 | Ashton |
| 2012/0277852 A1 | 11/2012 | Shukia et al. |
| 2013/0122096 A1 | 5/2013 | Shemi et al. |
| 2013/0189342 A1 | 7/2013 | Patel et al. |
| 2013/0195951 A1 | 8/2013 | Patel et al. |
| 2013/0202673 A1 | 8/2013 | Patel et al. |
| 2013/0218081 A1 | 8/2013 | Roth |
| 2013/0273137 A1 | 10/2013 | Mandell et al. |
| 2013/0287688 A1 | 10/2013 | Jain et al. |
| 2014/0037746 A1 | 2/2014 | Ashton et al. |
| 2014/0086995 A1 | 3/2014 | Ratner et al. |
| 2014/0088131 A1 | 3/2014 | Patel et al. |
| 2014/0094407 A1 | 4/2014 | Ron et al. |
| 2014/0127228 A1 | 5/2014 | Marks et al. |
| 2014/0209100 A1 | 7/2014 | Kiser et al. |
| 2014/0212355 A1 | 7/2014 | Trollsas et al. |
| 2014/0234381 A1 | 8/2014 | Tao et al. |
| 2014/0234389 A1 | 8/2014 | Shiah et al. |
| 2014/0271765 A1 | 9/2014 | Patel |
| 2014/0314966 A1 | 10/2014 | Fink et al. |
| 2014/0328884 A1 | 11/2014 | Reyes et al. |
| 2014/0363484 A1 | 12/2014 | Koyakutty et al. |
| 2015/0004213 A1 | 1/2015 | Ron |
| 2015/0017250 A1* | 1/2015 | Wening ............... A61K 31/137 424/501 |
| 2015/0140062 A1 | 5/2015 | Shiah et al. |
| 2015/0190348 A1 | 7/2015 | Haksar et al. |
| 2015/0209488 A1 | 7/2015 | Siegel et al. |
| 2015/0230971 A1 | 8/2015 | Wildemeersch |
| 2015/0297509 A1 | 10/2015 | Schwarz |
| 2015/0306230 A1 | 10/2015 | Combs et al. |
| 2015/0342894 A1 | 12/2015 | Anderson |
| 2015/0366825 A1 | 12/2015 | Joshi et al. |
| 2016/0008399 A1 | 1/2016 | Stephan |
| 2016/0022571 A1 | 1/2016 | Schwarz et al. |
| 2016/0067071 A1 | 3/2016 | Jose et al. |
| 2016/0081933 A1 | 3/2016 | Hensel et al. |
| 2016/0143844 A1 | 5/2016 | Carrasquillo et al. |
| 2016/0206633 A1 | 7/2016 | Barth et al. |
| 2016/0302965 A1 | 10/2016 | Erickson et al. |
| 2017/0121513 A1 | 5/2017 | Zhang et al. |
| 2017/0246117 A1 | 8/2017 | Helliwell et al. |
| 2018/0125780 A1 | 5/2018 | Grattoni et al. |
| 2018/0140556 A1 | 5/2018 | Joshi et al. |
| 2018/0214507 A1 | 8/2018 | Kacker et al. |
| 2018/0256606 A1 | 9/2018 | Petereit et al. |
| 2018/0280194 A1 | 10/2018 | Heitzmann et al. |
| 2018/0333296 A1 | 11/2018 | Heitzmann et al. |
| 2019/0046434 A1 | 2/2019 | Mota Leite Machado Mariz et al. |
| 2019/0112354 A1 | 4/2019 | Forsayeth et al. |
| 2019/0184145 A1 | 6/2019 | Munster et al. |
| 2019/0307885 A1 | 10/2019 | Zugates et al. |
| 2019/0358167 A1 | 11/2019 | Schneider |
| 2020/0000976 A1 | 1/2020 | Jeffery |
| 2020/0093852 A1 | 3/2020 | Nelms et al. |
| 2020/0113829 A1 | 4/2020 | Chang et al. |
| 2020/0138707 A1 | 5/2020 | McGinity et al. |
| 2020/0138729 A1 | 5/2020 | Schwartz et al. |
| 2020/0179374 A1 | 6/2020 | Orefice et al. |
| 2020/0197327 A1 | 6/2020 | Wening et al. |
| 2020/0316159 A1 | 10/2020 | Ghatnekar |
| 2021/0007973 A1 | 1/2021 | Patel et al. |

(56) References Cited

U.S. PATENT DOCUMENTS

| | | | |
|---|---|---|---|
| 2021/0113664 A1 | 4/2021 | Patel et al. | |
| 2021/0177742 A1 | 6/2021 | Patel | |

FOREIGN PATENT DOCUMENTS

| | | | | |
|---|---|---|---|---|
| CN | 101011345 A | 8/2007 | | |
| CN | 101385698 A | 3/2009 | | |
| CN | 103435424 B | 3/2016 | | |
| DE | 102013011399 A1 | 2/2014 | | |
| EP | 0 290 891 A1 | 11/1988 | | |
| EP | 2 265 293 B1 | 11/2015 | | |
| JP | H 10230148 A | 9/1998 | | |
| KR | 20210010226 A | 1/2021 | | |
| UA | 103635 C2 | 11/2013 | | |
| WO | WO02062352 A2 | 8/2002 | | |
| WO | WO 2006/063242 A1 | 6/2006 | | |
| WO | WO 2009129459 A1 | 10/2009 | | |
| WO | WO 2010/133757 A1 | 11/2010 | | |
| WO | WO 2010/133761 A1 | 11/2010 | | |
| WO | WO-2011116132 A1 | * | 9/2011 | ........... A61K 31/198 |
| WO | WO 2013/178811 A1 | 12/2013 | | |
| WO | WO 2013/178812 A1 | 12/2013 | | |
| WO | WO 2014/160026 A2 | 10/2014 | | |
| WO | WO 2016/064959 A1 | 4/2016 | | |
| WO | WO 2016/079204 A1 | 5/2016 | | |
| WO | WO 2016/180764 A1 | 11/2016 | | |
| WO | WO 2018/067882 A1 | 4/2018 | | |
| WO | WO 2019/213128 A1 | 11/2019 | | |
| WO | WO 2020/006240 A1 | 1/2020 | | |
| WO | WO 2020/041500 A1 | 2/2020 | | |
| WO | WO 2020/198737 A1 | 10/2020 | | |
| WO | WO2021122822 A1 | 6/2021 | | |

OTHER PUBLICATIONS

Ahmed et al., "Recent Advances in Polymeric Implants," *AAPS PharmSciTech*, (2019) 20: 300, 10 pages.

Bix et al, "Elvax as a slow-release delivery agent for a platelet-activating factor receptor agonist and antagonist," *Journal of Neuroscience Methods*, 77, 1997, pp. 67-74.

Bloch et al., "Nerve Growth Factor- and Neurotrophin-3-Releasing Guidance Channels Promote Regeneration of the Transected Rat Dorsal Root," *Experimental Neurology 172*, 2001, pp. 425-432.

Daukss et al., "Microscale implantable drug delivery systems: emerging IP strategies," *News & Analysis Biobusiness Briefs*, Nature Reviews, Drug Discovery, Nov. 2016, vol. 15, pp. 740-741.

Doughty et al., "Short Communication - Neurotrophin-3 promotes cerebellar granulate cell exit from the EGL." *European Journal of Neuroscience*, vol. 10, 1998, pp. 3007-3011.

Feng et al., "Twin-screw extrusion of sustained-release oral dosage forms and medical implants," *Drug Delivery and Translations Research*, 2018, 8, pp. 1694-1713.

Jong et al, "Controlled release of plasmid DNA," *Journal of Controlled Release*, Release 47, 1997, pp. 123-134.

Kimball et al., "A novel approach to administration of peptides in women: Systemic absorption of a GnRH agonist vial transvaginal ring delivery system," *Journal of Controlled Release 233*, 2016, pp. 19-28.

Kuo-Haller et al., "Vaccine delivery by polymeric vehicles in the mouse reproductive tract induce sustained local and systemic immunity," *Mol. Pharm.*, Oct. 4, 2010, 7(5), pp. 1585-1595.

Langer et al., "Polymers for the sustained release of proteins and other macromolecules," *Nature*, vol. 263, pp. 797-800.

Loxley, Andrew, "Hot Melt-Extrusion in the Production of Intravaginal Rings Containing Antiretroviral Drugs," *ANTEC 2010*, May 18, 2010, 28 pages.

Master Dissertation of Pharm. Kristof Dhaenens entitled "Ethylene Vinyl Acetate as Matrix for Oral Sustained Release Multiple-Unit Dosage Forms Produced via Hot-Melt Extrusion," 2009-2010, Universiteit Gent, Department of Pharmaceutics, 61 pages.

Paper—Stanković et al., "Polymeric formulations for drug release prepared by Hot Melt Extrusion, Application and characterization," pp. 16-49.

Preis et al., "Short Communication—A Single-Step Immunization by Sustained Antigen Release," *Journal of Immunological Methods*, 28, 1979, pp. 193-197.

Ramgopal et al., "Sustained Release of Complexed and Naked DNA from Polymer Films," *Journal of Biomedical Materials Research Part B: Applied Biomaterials*, 2007, pp. 496-503.

Saltzman et al, "Intracranial Delivery of Recombinant Nerve Growth Factor: Release Kinetics and Protein Distribution for Three Delivery Systems," *Pharmaceutical Research*, vol. 16, No. 2, 1999, pp. 232-240.

Saltzman et al., "Transport rates of proteins in porous materials with known microgeometry," *Biophys. J. (Biophysical Society)*, vol. 55, Jan. 1989, pp. 163-171.

Schneider et al., "Applications of ethylene vinyl acetate copolymers (EVA) in drug delivery systems," *Journal of Controlled Release 262*, 2017, pp. 284-295.

Shin et al., "Controlled release of triprolidine using ethylene-vinyl acetate membrane and matrix systems," *European Journal of Pharmaceutics and Biopharmaceutics 54*, May 5, 2002, pp. 201-206.

Supplementary European Search Report for EP 19 80 6736 dated Jan. 20, 2022, 11 pages.

Supplementary Search Report for EP 19 80 6504 dated Feb. 15, 2022, 18 pages.

International Search Report and Written Opinion for PCT/US2019/033063 dated Jul. 19, 2019, 11 pages.

Elvax 760, obtained from WayBack Machine https://web.archive.org/web/20210122035942/https://www.dow.com/en-us/pdp.elvax-760-ethylene-vinyl-acetate-copolymer.1893165z.html#properties on May 15, 2024, published Jan. 22, 2021, (Year:2021).

* cited by examiner

IMPLANTABLE DEVICE FOR SUSTAINED RELEASE OF A MACROMOLECULAR DRUG COMPOUND

RELATED APPLICATIONS

The present application is a continuation of U.S. application Ser. No. 16/416,328 (filed on May 20, 2019), which claims priority to U.S. Application Ser. No. 62/675,994 (filed on May 24, 2018), which are incorporated herein in their entirety by reference thereto.

BACKGROUND OF THE INVENTION

Biologic macromolecule drug compounds are typically composed of one or more oligomeric or polymeric chains, forming a three-dimensional structure held together by non-covalent forces. While these drug compounds have the potential for a multitude of therapeutic benefits, it has been traditionally difficult to controllably deliver these compounds over a sustained period of time. Many implantable delivery devices, for example, are formed by solubilizing a drug compound into a matrix polymer. These solubilized drug molecules can diffuse through the implant and be released into a patient. Unfortunately, however, drug elution is highly dependent upon the diffusion coefficient of the drug molecule, which in turn, is inversely proportional to the molecular weight of the drug molecule. Thus, macromolecular drug compounds tend to have a lower diffusion coefficient due to their larger molecular weight. Further, such compounds often have chain length entanglements, which can even further reduce the effective diffusion coefficient. In light of these difficulties, a need continues to exist for an implantable delivery device that is capable of delivering a macromolecular compound in effective amounts over a sustained period of time.

SUMMARY OF THE INVENTION

In accordance with one embodiment of the present invention, an implantable device for delivery of a macromolecular drug compound is disclosed. The device comprises a core having an outer surface and a membrane layer positioned adjacent to the outer surface of the core. The core comprises a core polymer matrix within which is dispersed a drug compound having a molecular weight of about 0.5 kDa or more, the polymer matrix containing a hydrophobic polymer. Further, the membrane layer comprises a membrane polymer matrix within which the macromolecular drug compound is optionally dispersed, wherein the membrane polymer matrix contains a hydrophobic polymer in combination with a hydrophilic compound. The weight ratio of the hydrophobic polymer to the hydrophilic compound within the membrane polymer matrix ranges from about 0.25 to about 200.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended drawings in which.

Figure 1:
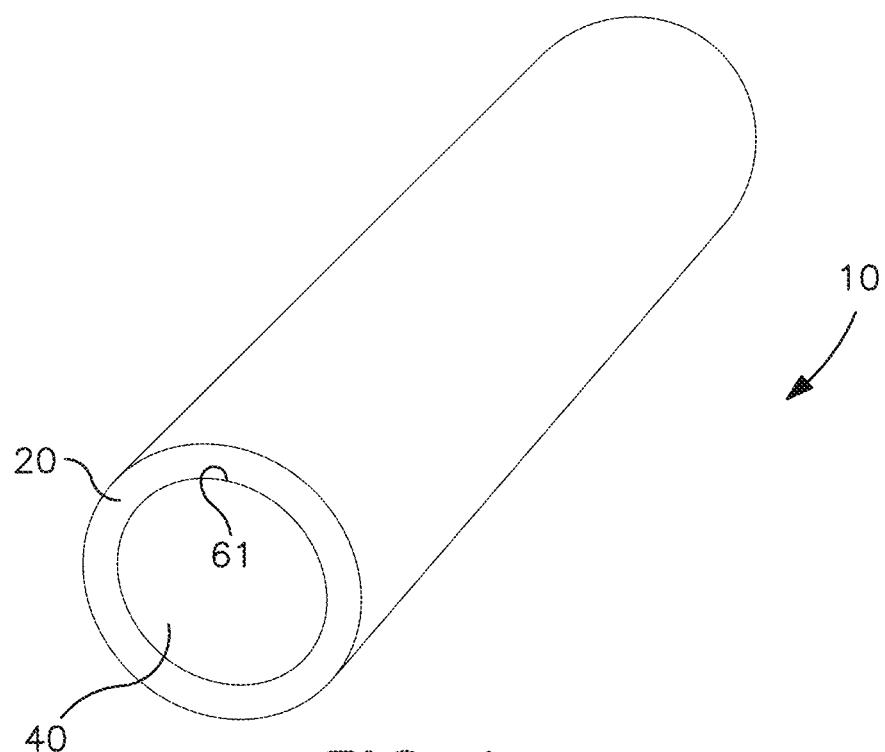
FIG. 1 is a perspective view of one embodiment of the implantable device of the present invention.

Repeat use of references characters in the present specification and drawing is intended to represent same or analogous features or elements of the invention.

DETAILED DESCRIPTION

It is to be understood by one of ordinary skill in the art that the present discussion is a description of exemplary embodiments only, and is not intended as limiting the broader aspects of the present invention.

Generally speaking, the present invention is directed to an implantable device that is capable of delivering a macromolecular drug compound for prohibiting and/or treating a condition, disease, and/or cosmetic state in a patient (e.g., human, pet, farm animal, race horse, etc.). The implantable device may have a variety of different geometric shapes, such as cylindrical (rod), disc, ring, doughnut, helical, elliptical, triangular, ovular, etc. In one embodiment, for example, the device may have a generally circular cross-sectional shape so that the overall structure is in the form of a cylinder (rod) or disc. In such embodiments, the device will typically have a diameter of from about 0.5 to about 50 millimeters, in some embodiments from about 1 to about 40 millimeters, and in some embodiments, from about 5 to about 30 millimeters. The length of the device may vary, but is typically in the range of from about 1 to about 25 millimeters. Cylindrical devices may, for instance, have a length of from about 5 to about 50 millimeters, while disc-shaped devices may have a length of from about 0.5 to about 5 millimeters.

Regardless of the particular shape or size, the device is multilayered in that it contains at least one membrane layer positioned adjacent to an outer surface of a core. The core contains a core polymer matrix that includes a hydrophobic polymer and a macromolecular drug compound that is dispersed within the core polymer matrix. Typically, macromolecular drug compounds will constitute from about 5 wt. % to about 60 wt. %, in some embodiments from about 10 wt. % to about 50 wt. %, and in some embodiments, from about 15 wt. % to about 45 wt. % of the core, while the core polymer matrix constitutes from about 40 wt. % to about 95 wt. %, in some embodiments from about 50 wt. % to about 90 wt. %, and in some embodiments, from about 55 wt. % to about 85 wt. % of the core. The membrane layer(s) also contain a membrane polymer matrix within which a drug compound may optionally be dispersed. The membrane polymer matrix contains a combination of a hydrophobic polymer and a hydrophilic compound (e.g., hydrophilic polymer) that is soluble and/or swellable in water. To help achieve the desired release of the macromolecular drug compound, the weight ratio of the hydrophobic polymers to the hydrophilic compounds within the membrane polymer matrix is selectively controlled, such as within a range of from about 0.25 to about 200, in some embodiments from about 0.4 to about 80, in some embodiments from about 0.8 to about 20, in some embodiments from about 1 to about 16, and in some embodiments, from about 1.2 to about 10.

Through selective control over the particular nature of the core and membrane layer(s) as noted above, and the manner in which they are formed, the present inventors have discovered that the resulting device can be effective for sustained release over a macromolecular drug compound over a prolonged period of time. For example, the implantable device can release the drug compound for a time period of about 5 days or more, in some embodiments about 10 days or more, in some embodiments from about 20 days to about 60 days, and in some embodiments, from about 25 days to about 50 days (e.g., about 30 days). Further, the present inventors have also discovered that the drug compound can be released in a controlled manner (e.g., zero order or near zero order) over the course of the release time period. After a time period of 15 days, for example, the cumulative release ratio of the implantable device may be from about 20% to about 70%, in some embodiments from about 30% to about 65%, and in some embodiments, from about 40% to about 60%. Likewise, after a time period of 30 days, the cumulative release ratio of the implantable device may still be from about 40% to about 85%, in some embodiments from about 50% to about 80%, and in some embodiments, from about 60% to about 80%. The "cumulative release ratio" may be determined by dividing the amount of the drug compound released at a particulate time interval by the total amount of drug compound initially present, and then multiplying this number by 100.

Of course, the actual dosage level of the drug compound delivered will vary depending on the particular drug compound employed and the time period for which it is intend to be released. The dosage level is generally high enough to provide a therapeutically effective amount of the drug compound to render a desired therapeutic outcome, i.e., a level or amount effective to reduce or alleviate symptoms of the condition for which it is administered. The exact amount necessary will vary, depending on the subject being treated, the age and general condition of the subject to which the macromolecular drug compound is to be delivered, the capacity of the subject's immune system, the degree of effect desired, the severity of the condition being treated, the particular macromolecular drug compound selected and mode of administration of the composition, among other factors. An appropriate effective amount can be readily determined by one of skill in the art. For example, an effective amount will typically range from about 5 µg to about 200 mg, in some embodiments from about 5 µg to about 100 mg per day, and in some embodiments, from about 10 µg to about 1 mg of the macromolecular drug compound delivered per day.

Various embodiments of the present invention will now be described in more detail.

I. Core

As indicated above, the core polymer matrix contains at least polymer that is generally hydrophobic in nature so that it can retain its structural integrity for a certain period of time when placed in an aqueous environment, such as the body of a mammal, and stable enough to be stored for an extended period before use. Examples of suitable hydrophobic polymers for this purpose may include, for instance, silicone polymer, polyolefins, polyvinyl chloride, polycarbonates, polysulphones, styrene acrylonitrile copolymers, polyurethanes, silicone polyether-urethanes, polycarbonate-urethanes, silicone polycarbonate-urethanes, etc., as well as combinations thereof. Of course, hydrophilic polymers that are coated or otherwise encapsulated with a hydrophobic polymer are also suitable for use in the core polymer matrix. Typically, the melt flow index of the hydrophobic polymer ranges from about 0.2 to about 100 g/10 min, in some embodiments from about 5 to about 90 g/10 min, in some embodiments from about 10 to about 80 g/10 min, and in some embodiments, from about 30 to about 70 g/10 min, as determined in accordance with ASTM D1238-13 at a temperature of 190° C. and a load of 2.16 kilograms.

In certain embodiments, the core polymer matrix may contain a semi-crystalline olefin copolymer. The melting temperature of such an olefin copolymer may, for instance, range from about 40° C. to about 140° C., in some embodiments from about 50° C. to about 125° C., and in some embodiments, from about 60° C. to about 120° C., as determined in accordance with ASTM D3418-15. Such copolymers are generally derived from at least one olefin monomer (e.g., ethylene, propylene, etc.) and at least one polar monomer that is grafted onto the polymer backbone and/or incorporated as a constituent of the polymer (e.g., block or random copolymers). Suitable polar monomers include, for instance, a vinyl acetate, vinyl alcohol, maleic anhydride, maleic acid, (meth)acrylic acid (e.g., acrylic acid, methacrylic acid, etc.), (meth)acrylate (e.g., acrylate, methacrylate, ethyl acrylate, methyl methacrylate, ethyl methacrylate, etc.), and so forth. A wide variety of such copolymers may generally be employed in the polymer composition, such as ethylene vinyl acetate copolymers, ethylene (meth)acrylic acid polymers (e.g., ethylene acrylic acid copolymers and partially neutralized ionomers of these copolymers, ethylene methacrylic acid copolymers and partially neutralized ionomers of these copolymers, etc.), ethylene (meth)acrylate polymers (e.g., ethylene methylacrylate copolymers, ethylene ethyl acrylate copolymers, ethylene butyl acrylate copolymers, etc.), and so forth. Regardless of the particular monomers selected, the present inventors have discovered that certain aspects of the copolymer can be selectively controlled to help achieve the desired release properties. For instance, the polar monomeric content of the copolymer may be selectively controlled to be within a range of from about 10 wt. % to about 60 wt. %, in some embodiments about 20 wt. % to about 55 wt. %, and in some embodiments, from about 25 wt. % to about 50 wt. %. Conversely, the olefin monomeric content of the copolymer may be likewise be within a range of from about 40 wt. % to about 90 wt. %, in some embodiments about 45 wt. % to about 80 wt. %, and in some embodiments, from about 50 wt. % to about 75 wt. %.

In one particular embodiment, for example, the core polymer matrix may contain an ethylene vinyl acetate polymer, which is a copolymer that is derived from at least one ethylene monomer and at least one vinyl acetate monomer. The density of the ethylene vinyl acetate copolymer may also range from about 0.900 to about 1.00 gram per cubic centimeter (g/cm$^3$), in some embodiments from about 0.910 to about 0.980 g/cm$^3$, and in some embodiments, from about 0.940 to about 0.970 g/cm$^3$, as determined in accordance with ASTM D1505-10. Examples of suitable ethylene vinyl acetate copolymers that may be employed include those available from Celanese under the designation ATEVA® (e.g., ATEVA® 4030AC); DuPont under the designation ELVAX® (e.g., ELVAX® 40 W); and Arkema under the designation EVATANE® (e.g., EVATANE 40-55). Any of a variety of techniques may generally be used to form the ethylene vinyl acetate copolymer with the desired properties as is known in the art. In one embodiment, the polymer is produced by copolymerizing an ethylene monomer and a vinyl acetate monomer in a high pressure reaction. Vinyl acetate may be produced from the oxidation of butane to yield acetic anhydride and acetaldehyde, which can react together to form ethylidene diacetate. Ethylidene diacetate can then be thermally decomposed in the presence of an acid catalyst to form the vinyl acetate monomer. Examples of suitable acid catalysts include aromatic sulfonic acids (e.g., benzene sulfonic acid, toluene sulfonic acid, ethylbenzene sulfonic acid, xylene sulfonic acid, and naphthalene sulfonic acid), sulfuric acid, and alkanesulfonic acids, such as described in U.S. Pat. No. 2,425,389 to Oxley et al; U.S. Pat. No. 2,859,241 to Schnizer; and U.S. Pat. No. 4,843,170 to Isshiki et al. The vinyl acetate monomer can also be produced by reacting acetic anhydride with hydrogen in the presence of a catalyst instead of acetaldehyde. This process converts vinyl acetate directly from acetic anhydride and hydrogen without the need to produce ethylidene diacetate. In yet another embodiment, the vinyl acetate monomer can be produced from the reaction of acetaldehyde and a ketene in the presence of a suitable solid catalyst, such as a perfluorosulfonic acid resin or zeolite.

One or more drug compounds are also be dispersed within the core polymer matrix that are capable of prohibiting and/or treating a condition, disease, and/or cosmetic state a patient. The drug compound may be prophylactically, therapeutically, and/or cosmetically active, systemically or locally. Regardless, at least one drug compound within the core is a "macromolecular" compound in the sense that it has a large molecular weight, such as about 0.5 kilodaltons ("kDa") or more, in some embodiments about 1 kDa or more, in some embodiments from about 5 kDa to about 250 kDa, and in some embodiments, from about 20 kDa to about 200 kDa. Typically, the bioactivity of such compounds depends upon a unique three-dimensional (e.g., folded) structure of the molecule. This three-dimensional molecular structure is substantially maintained by specific non-covalent bonding interactions, such as hydrogen bonding and hydrophobic bonding interactions between atoms (hydrophobicity). The drug compound can be either naturally occurring or man-made by any method known in the art.

Typically, it is also desired that the drug compound is stable at high temperatures so that it can be incorporated into the polymer matrix at or near the melting temperature of the hydrophobic polymer employed in the core polymer matrix. For example, the drug compound typically remains stable at temperatures of from about 25° C. to about 120° C., in some embodiments from about 40° C. to about 110° C., in some embodiments from about 40° C. to about 100° C., in some embodiments from about 40° C. to about 80° C., and in some embodiments, from about 50° C. to about 70° C.

Particular examples of suitable macromolecular drug compounds may include, for instance, proteins, peptides, enzymes, antibodies, interferons, interleukins, blood factors, vaccines, nucleotides, lipids, etc., as well as analogues, derivatives, and combinations thereof. Suitable proteins or peptides may include, for instance, adrenocorticotropic hormone, angiotensin, beta-endorphin, bombesin, calcitonin, calcitonin gene relating polypeptide, cholecystokinin-8, colony stimulating factors, desmopressin, endothelin, enkephalin, erythropoietins, gastrins, glucagon, human atrial natriuretic polypeptide, interferons, insulin, growth factors, growth hormones, luteinizing hormone release hormone, melanocyte stimulating hormone, muramyl-dipeptide, neurotensin, oxytocin, parathyroid hormone, peptide T, secretin, somatomedins, somatostatin, thyroid stimulating hormone, thyrotropin releasing hormone, thyrotropin stimulating hormone, vasoactive intestinal polypeptide, vasopressin, etc. Suitable antibodies (e.g., monoclonal antibodies) may include, without limitation, HIV monoclonal antibody 2F5, rituximab, infliximab, trastuzumab, adalimumab, omalizumab, tositumomab, efalizumab, and cetuximab. Suitable interferons may include interferon alpha-2b, peg interferon alpha-2b, interferon alpha-2b+ribavirin, interferon alpha-2a, pegylated interferon alpha-2a, interferon beta-1a, and interferon beta. Suitable blood factors may include alteplase/tenecteplase and rhesus factor Vila. Suitable interleukins may include interleukin-2. Suitable vaccines may include whole viral particles, recombinant proteins, subunit proteins such as gp41, gp120 and gp140, DNA vaccines, plasmids, bacterial vaccines, polysaccharides such as extracellular capsular polysaccharides, and other vaccine vectors. Likewise, suitable nucleic acids may include RNA- or DNA-based molecules, such as oligonucleotides, aptamers, ribozymes, DNAzymes and small interfering RNAs, such as messenger (mRNA), transfer (tRNA), ribosomal (rRNA), interfering (iRNA), small interfering (siRNA), etc.

The core may also optionally contain one or more excipients if so desired, such as radiocontrast agents, release modifiers, bulking agents, plasticizers, surfactants, cross-linking agents, flow aids, colorizing agents (e.g., chlorophyll, methylene blue, etc.), antioxidants, stabilizers, lubricants, other types of antimicrobial agents, preservatives, etc. to enhance properties and processability. When employed, the optional excipient(s) typically constitute from about 0.01 wt. % to about 20 wt. %, and in some embodiments, from about 0.05 wt. % to about 15 wt. %, and in some embodiments, from about 0.1 wt. % to about 10 wt. % of the core. In one embodiment, for instance, a radiocontrast agent may be employed to help ensure that the device can be detected in an X-ray based imaging technique (e.g., computed tomography, projectional radiography, fluoroscopy, etc.). Examples of such agents include, for instance, barium-based compounds, iodine-based compounds, zirconium-based compounds (e.g., zirconium dioxide), etc. One particular example of such an agent is barium sulfate. Other known antimicrobial agents and/or preservatives may also be employed to help prevent surface growth and attachment of bacteria, such as metal compounds (e.g., silver, copper, or zinc), metal salts, quaternary ammonium compounds, etc.

Regardless of the particular components employed, the core may be formed through a variety of known techniques, such as by hot-melt extrusion, injection molding, solvent casting, dip coating, spray coating, microextrusion, coacervation, etc. In one embodiment, a hot-melt extrusion technique may be employed. Hot-melt extrusion is generally a solvent-free process in which the components of the core (e.g., hydrophobic polymer, drug compound(s), optional excipients, etc.) may be melt blended and optionally shaped in a continuous manufacturing process to enable consistent output quality at high throughput rates. This technique is particularly well suited to various types of hydrophobic polymers, such as olefin copolymers. Namely, such copolymers typically exhibit a relatively high degree of long-chain branching with a broad molecular weight distribution. This combination of traits can lead to shear thinning of the copolymer during the extrusion process, which help facilitates hot-melt extrusion. Furthermore, the polar comonomer units (e.g., vinyl acetate) can serve as an "internal" plasticizer by inhibiting crystallization of the polyethylene chain segments. This may lead to a lower melting point of the olefin copolymer, which improves the overall flexibility of the resulting material and enhances its ability to be formed into devices of a wide variety of shapes and sizes.

During a hot-melt extrusion process, melt blending may occur at a temperature range of from about 40° C. to about 200° C., in some embodiments, from about 60° C. to about 180° C., and in some embodiments, from about 80° C. to about 150° C. to form a polymer composition. Any of a variety of melt blending techniques may generally be employed. For example, the components may be supplied separately or in combination to an extruder that includes at least one screw rotatably mounted and received within a barrel (e.g., cylindrical barrel). The extruder may be a single screw or twin screw extruder. For example, one embodiment of a single screw extruder may contain a housing or barrel and a screw rotatably driven on one end by a suitable drive (typically including a motor and gearbox). If desired, a twin-screw extruder may be employed that contains two separate screws. The configuration of the screw is not particularly critical and it may contain any number and/or orientation of threads and channels as is known in the art. For example, the screw typically contains a thread that forms a generally helical channel radially extending around a core of the screw. A feed section and melt section may be defined along the length of the screw. The feed section is the input portion of the barrel where the olefin copolymer(s) and/or drug compound(s) are added. The melt section is the phase change section in which the copolymer is changed from a solid to a liquid-like state. While there is no precisely defined delineation of these sections when the extruder is manufactured, it is well within the ordinary skill of those in this art to reliably identify the feed section and the melt section in which phase change from solid to liquid is occurring. Although not necessarily required, the extruder may also have a mixing section that is located adjacent to the output end of the barrel and downstream from the melting section. If desired, one or more distributive and/or dispersive mixing elements may be employed within the mixing and/or melting sections of the extruder. Suitable distributive mixers for single screw extruders may include, for instance, Saxon, Dulmage, Cavity Transfer mixers, etc. Likewise, suitable dispersive mixers may include Blister ring, Leroy/Maddock, CRD mixers, etc. As is well known in the art, the mixing may be further improved by using pins in the barrel that create a folding and reorientation of the polymer melt, such as those used in Buss Kneader extruders, Cavity Transfer mixers, and Vortex Intermeshing Pin mixers.

If desired, the ratio of the length ("L") to diameter ("D") of the screw may be selected to achieve an optimum balance between throughput and blending of the components. The L/D value may, for instance, range from about 10 to about 50, in some embodiments from about 15 to about 45, and in some embodiments from about 20 to about 40. The length of the screw may, for instance, range from about 0.1 to about 5 meters, in some embodiments from about 0.4 to about 4 meters, and in some embodiments, from about 0.5 to about 2 meters. The diameter of the screw may likewise be from about 5 to about 150 millimeters, in some embodiments from about 10 to about 120 millimeters, and in some embodiments, from about 20 to about 80 millimeters. In addition to the length and diameter, other aspects of the extruder may also be selected to help achieve the desired degree of blending. For example, the speed of the screw may be selected to achieve the desired residence time, shear rate, melt processing temperature, etc. For example, the screw speed may range from about 10 to about 800 revolutions per minute ("rpm"), in some embodiments from about 20 to about 500 rpm, and in some embodiments, from about 30 to about 400 rpm. The apparent shear rate during melt blending may also range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows.

Once melt blended together, the resulting polymer composition may be in the form of pellets, sheets, fibers, filaments, etc., which may be shaped into the core using a variety of known shaping techniques, such as injection molding, compression molding, nanomolding, overmolding, blow molding, three-dimensional printing, etc. Injection molding may, for example, occur in two main phases—i.e., an injection phase and holding phase. During the injection phase, a mold cavity is filled with the molten polymer composition. The holding phase is initiated after completion of the injection phase in which the holding pressure is controlled to pack additional material into the cavity and compensate for volumetric shrinkage that occurs during cooling. After the shot has built, it can then be cooled. Once cooling is complete, the molding cycle is completed when the mold opens and the part is ejected, such as with the assistance of ejector pins within the mold. Any suitable injection molding equipment may generally be employed in the present invention. In one embodiment, an injection molding apparatus may be employed that includes a first mold base and a second mold base, which together define a mold cavity having the shape of the core. The molding apparatus includes a resin flow path that extends from an outer exterior surface of the first mold half through a sprue to a mold cavity. The polymer composition may be supplied to the resin flow path using a variety of techniques. For example, the composition may be supplied (e.g., in the form of pellets) to a feed hopper attached to an extruder barrel that contains a rotating screw (not shown). As the screw rotates, the pellets are moved forward and undergo pressure and friction, which generates heat to melt the pellets. A cooling mechanism may also be provided to solidify the resin into the desired shape of the core (e.g., disc, rod, etc.) within the mold cavity. For instance, the mold bases may include one or more cooling lines through which a cooling medium flows to impart the desired mold temperature to the surface of the mold bases for solidifying the molten material. The mold temperature (e.g., temperature of a surface of the mold) may range from about 50° C. to about 120° C., in some embodiments from about 60° C. to about 110° C., and in some embodiments, from about 70° C. to about 90° C.

As indicated above, another suitable technique for forming a core of the desired shape and size is three-dimensional printing. During this process, the polymer composition may be incorporated into a printer cartridge that is readily adapted for use with a printer system. The printer cartridge may, for example, contains a spool or other similar device that carries the polymer composition. When supplied in the form of filaments, for example, the spool may have a generally cylindrical rim about which the filaments are wound. The spool may likewise define a bore or spindle that allows it to be readily mounted to the printer during use. Any of a variety of three-dimensional printer systems can be employed in the present invention. Particularly suitable printer systems are extrusion-based systems, which are often referred to as "fused deposition modeling" systems. For example, the polymer composition may be supplied to a build chamber of a print head that contains a platen and gantry. The platen may move along a vertical z-axis based on signals provided from a computer-operated controller. The gantry is a guide rail system that may be configured to move the print head in a horizontal x-y plane within the build chamber based on signals provided from controller. The print head is supported by the gantry and is configured for printing the build structure on the platen in a layer-by-layer manner, based on signals provided from the controller. For example, the print head may be a dual-tip extrusion head.

II. Membrane Layer

Figure 2:
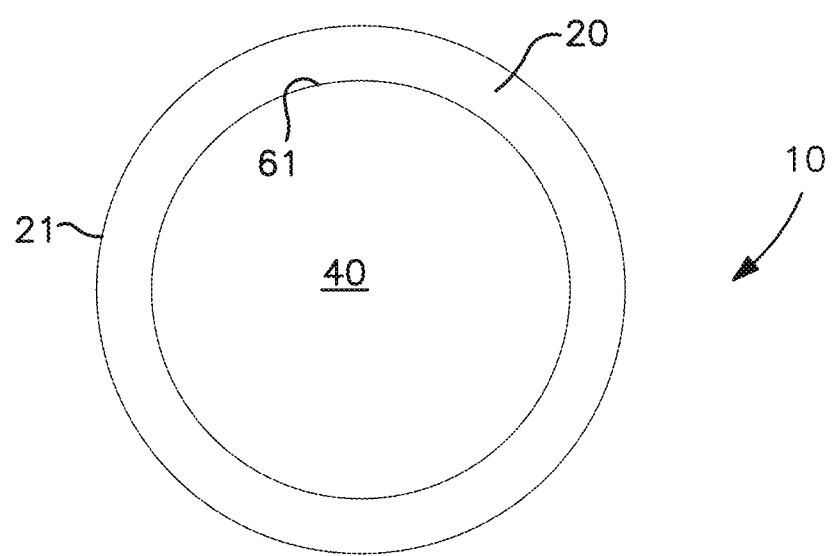
FIG. 2 is a cross-sectional view of the implantable device of FIG. 1.

As indicated above, the implantable device contains at least one membrane layer that is positioned adjacent to an outer surface of a core. The number of membrane layers may vary depending on the particular configuration of the device, the nature of the drug compound, and the desired release profile. For example, the device may contain only one membrane layer. Referring to FIGS. 1-2, for example, one embodiment of an implantable device 10 is shown that contains a core 40 having a generally circular cross-sectional shape and is elongated so that the resulting device is generally cylindrical in nature. The core 40 defines an outer circumferential surface 61 about which a membrane layer 20 is circumferentially disposed. Similar to the core 40, the membrane layer 20 also has a generally circular cross-sectional shape and is elongated so that it covers the entire length of the core 40. During use of the device 10, a drug compound is capable of being released from the core 40 and through the membrane layer 20 so that it exits from an external surface 21 of the device.

Figure 3:
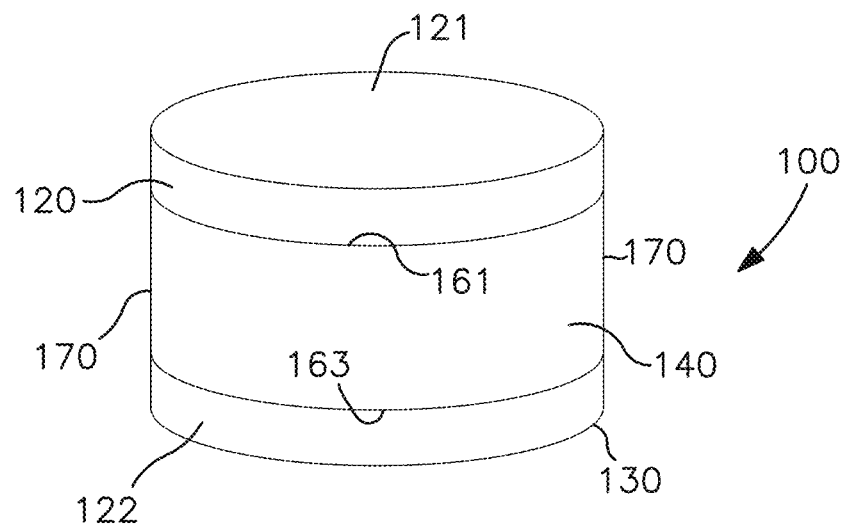
FIG. 3 is a perspective view of another embodiment of the implantable device of the present invention.
Figure 4:
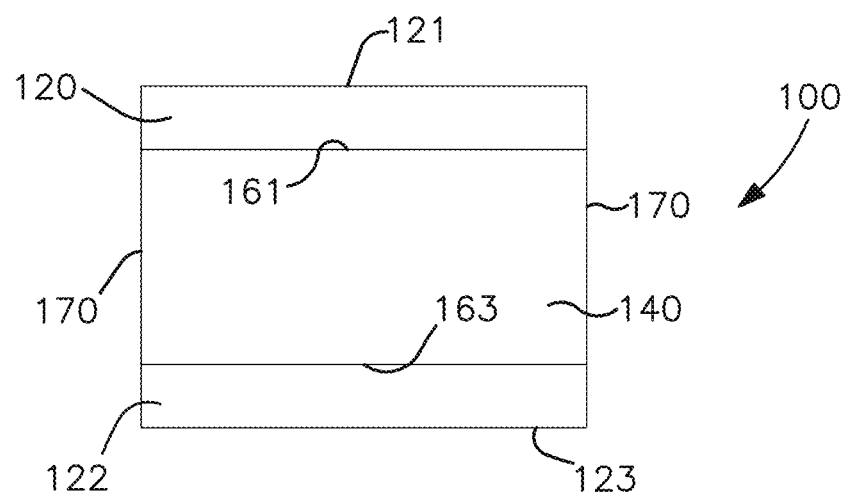
FIG. 4 is a cross-sectional view of the implantable device of FIG. 3.

Of course, in other embodiments, the device may contain multiple membrane layers. In the device of FIGS. 1-2, for example, one or more additional membrane layers (not shown) may be disposed over the membrane layer 20 to help further control release of the drug compound. In other embodiments, the device may be configured so that the core is positioned or sandwiched between separate membrane layers. Referring to FIGS. 3-4, for example, one embodiment of an implantable device 100 is shown that contains a core 140 having a generally circular cross-sectional shape and is elongated so that the resulting device is generally disc-shaped in nature. The core 140 defines an upper outer surface 161 on which is positioned a first membrane layer 120 and a lower outer surface 163 on which is positioned a second membrane layer 122. Similar to the core 140, the first membrane layer 120 and the second membrane layer 122 also have a generally circular cross-sectional shape that generally covers the core 140. If desired, edges of the membrane layers 120 and 122 may also extend beyond the periphery of the core 140 so that they can be sealed together to cover any exposed areas of an external circumferential surface 170 of the core 140. During use of the device 100, a drug compound is capable of being released from the core 140 and through the first membrane layer 120 and second membrane layer 122 so that it exits from external surfaces 121 and 123 of the device. Of course, if desired, one or more additional membrane layers (not shown) may also be disposed over the first membrane layer 120 and/or second membrane layer 122 to help further control release of the drug compound.

Regardless of the particular configuration employed, the membrane layer(s) generally contain a membrane polymer matrix that contains a hydrophobic polymer and hydrophilic compound, such as described above. The polymer matrix typically constitutes from about 30 wt. % to 100 wt. %, in some embodiments, from about 40 wt. % to about 99 wt. %, and in some embodiments, from about 50 wt. % to about 90 wt. % of a membrane layer. As indicated above, the weight ratio of the hydrophobic polymers to the hydrophilic compounds within the membrane polymer matrix may range from about 0.8 to about 20, in some embodiments from about 1 to about 16, and in some embodiments, from about 1.2 to about 10. Such hydrophilic compounds may, for example, constitute from about 1 wt. % to about 50 wt. %, in some embodiments from about 2 wt. % to about 40 wt. %, and in some embodiments, from about 5 wt. % to about 30 wt. % of the membrane polymer matrix, while hydrophobic polymers typically constitute from about 50 wt. % to about 99 wt. %, in some embodiments from about 60 wt. % to about 98 wt. %, and in some embodiments, from about 70 wt. % to about 95 wt. % of the membrane polymer matrix. In such embodiments, hydrophilic compounds may likewise constitute from about 1 wt. % to about 50 wt. %, in some embodiments from about 2 wt. % to about 40 wt. %, and in some embodiments, from about 5 wt. % to about 30 wt. % of a membrane layer. Suitable hydrophilic compounds may include, for instance, polymers, non-polymeric materials (e.g., glycerin, sugars, salts, peptides, etc.), etc. Examples of suitable hydrophilic polymers include, for instance, sodium, potassium and calcium alginates, carboxymethylcellulose, agar, gelatin, polyvinyl alcohols, polyalkylene glycols (e.g., polyethylene glycol), collagen, pectin, chitin, chitosan, poly-1-caprolactone, polyvinylpyrrolidone, poly(vinylpyrrolidone-co-vinyl acetate), polysaccharides, hydrophilic polyurethane, polyhydroxyacrylate, dextran, xanthan, hydroxypropyl cellulose, methylcellulose, proteins, ethylene vinyl alcohol copolymers, water-soluble polysilanes and silicones, water-soluble polyurethanes, etc., as well as combinations thereof. Particularly suitable hydrophilic polymers are polyalkylene glycols, such as those having a molecular weight of from about 100 to 500,000 grams per mole, in some embodiments from about 500 to 200,000 grams per mole, and in some embodiments, from about 1,000 to about 100,000 grams per mole. Specific examples of such polyalkylene glycols include, for instance, polyethylene glycols, polypropylene glycols polytetramethylene glycols, polyepichlorohydrins, etc.

When employing multiple membrane layers, it is typically desired that each membrane layer contains a polymer matrix that includes a hydrophobic polymer and hydrophilic compound. For example, a first membrane layer may contain a first membrane polymer matrix and a second membrane layer may contain a second membrane polymer matrix. In such embodiments, the first and second polymer matrices each contain a hydrophobic polymer and hydrophilic compound. The hydrophilic compound and hydrophobic polymer within one membrane layer may be the same or different than those employed in another membrane layer. In one embodiment, for instance, both the first and second polymer matrices employ the same hydrophilic compound (e.g., hydrophilic polymer) and hydrophobic polymer (e.g., α-olefin copolymer). Likewise, the hydrophobic polymer used in the membrane layer(s) may also be the same or different the hydrophobic polymer employed in the core. In one embodiment, for instance, both the core and the membrane layer(s) employ the same hydrophobic polymer (e.g., α-olefin copolymer). In yet other embodiments, the membrane layer(s) may employ a hydrophobic polymer (e.g., α-olefin copolymer) that has a lower melt flow index than a polymer employed in the core. Among other things, this can further help control the release of the drug compound from the device. For example, the ratio of the melt flow index of a hydrophobic polymer employed in the core to the melt flow index of a hydrophobic polymer employed in the membrane layer(s) may be from about 1 to about 20, in some embodiments about 2 to about 15, and in some embodiments, from about 4 to about 12. The melt flow index of the hydrophobic polymer in the membrane layer(s) may, for example, range from about 1 to about 80 g/10 min, in some embodiments from about 2 to about 70 g/10 min, and in some embodiments, from about 5 to about 60 g/10 min, as determined in accordance with ASTM D1238-13 at a temperature of 190° C. and a load of 2.16 kilograms. Examples of suitable ethylene vinyl acetate copolymers that may be employed include those available from Celanese under the designation ATEVA® (e.g., ATEVA® 4030AC or 2861A).

As indicated above, the membrane layer(s) used in the device may optionally contain a macromolecular drug compound, such as described above, which is dispersed within the polymer matrix. The drug compound in the membrane layer(s) may be the same or different than the drug compound employed in the core. Regardless, when such a macromolecular drug compound is employed in a membrane layer, the membrane layer generally contains the drug compound in an amount such that the ratio of the concentration (wt. %) of the drug compound in the core to the concentration (wt. %) of the drug compound in the membrane layer is greater than 1, in some embodiments about 1.5 or more, and in some embodiments, from about 1.8 to about 4. When employed, drug compounds typically constitute only from about 1 wt. % to about 40 wt. %, in some embodiments from about 5 wt. % to about 35 wt. %, and in some embodiments, from about 10 wt. % to about 30 wt. % of a membrane layer. Of course, in other embodiments, the membrane layer is generally free of such macromolecular drug compounds prior to release from the core. When multiple membrane layers are employed, each membrane layer may generally contains the drug compound in an amount such that the ratio of the weight percentage of the drug compound in the core to the weight percentage of the drug compound in the membrane layer is greater than 1, in some embodiments about 1.5 or more, and in some embodiments, from about 1.8 to about 4.

The membrane layer(s) and/or the core may also optionally contain one or more excipients as described above, such as radiocontrast agents, bulking agents, plasticizers, surfactants, crosslinking agents, flow aids, colorizing agents (e.g., chlorophyll, methylene blue, etc.), antioxidants, stabilizers, lubricants, other types of antimicrobial agents, preservatives, etc. to enhance properties and processability. When employed, the optional excipient(s) typically constitute from about 0.01 wt. % to about 60 wt. %, and in some embodiments, from about 0.05 wt. % to about 50 wt. %, and in some embodiments, from about 0.1 wt. % to about 40 wt. % of a membrane layer.

One or more nonionic, anionic, and/or amphoteric surfactants may also be employed to help create a uniform dispersion. When employed, such surfactant(s) typically constitute from about 0.05 wt. % to about 8 wt. %, and in some embodiments, from about 0.1 wt. % to about 6 wt. %, and in some embodiments, from about 0.5 wt. % to about 3 wt. % of the core. Nonionic surfactants, which typically have a hydrophobic base (e.g., long chain alkyl group or an alkylated aryl group) and a hydrophilic chain (e.g., chain containing ethoxy and/or propoxy moieties), are particularly suitable. Some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. Particularly suitable nonionic surfactants may include ethylene oxide condensates of fatty alcohols, polyoxyethylene ethers of fatty acids, polyoxyethylene sorbitan fatty acid esters, and sorbitan fatty acid esters, etc. The fatty components used to form such emulsifiers may be saturated or unsaturated, substituted or unsubstituted, and may contain from 6 to 22 carbon atoms, in some embodiments from 8 to 18 carbon atoms, and in some embodiments, from 12 to 14 carbon atoms. Sorbitan fatty acid esters (e.g., monoesters, diester, triesters, etc.) that have been modified with polyoxyethylene are one particularly useful group of nonionic surfactants. These materials are typically prepared through the addition of ethylene oxide to a 1,4-sorbitan ester. The addition of polyoxyethylene converts the lipophilic sorbitan ester surfactant to a hydrophilic surfactant that is generally soluble or dispersible in water. Such materials are commercially available under the designation TWEEN® (e.g., TWEEN® 80, or polyethylene (20) sorbitan monooleate).

The membrane layer(s) may be formed using the same or a different technique than used to form the core, such as by hot-melt extrusion, injection molding, solvent casting, dip coating, spray coating, microextrusion, coacervation, etc. In one embodiment, a hot-melt extrusion technique may be employed. The core and membrane layer(s) may also be formed separately or simultaneously. In one embodiment, for instance, the core and membrane layer(s) are separately formed and then combined together using a known bonding technique, such as by stamping, hot sealing, adhesive bonding, etc.

III. Use of Device

The implantable device of the present invention may be used in a variety of different ways to treat prohibit and/or treat a condition, disease, or cosmetic state in a patient. The device may be implanted subcutaneously, orally, mucosally, etc., using standard techniques. The delivery route may be intrapulmonary, gastroenteral, subcutaneous, intramuscular, or for introduction into the central nervous system, intraperitoneum or for intraorgan delivery. If desired, the device may be sealed within a package (e.g., sterile blister package) prior to use. The materials and manner in which the package is sealed may vary as is known in the art. In one embodiment, for instance, the package may contain a substrate that includes any number of layers desired to achieve the desired level of protective properties, such as 1 or more, in some embodiments from 1 to 4 layers, and in some embodiments, from 1 to 3 layers. Typically, the substrate contains a polymer film, such as those formed from a polyolefin (e.g., ethylene copolymers, propylene copolymers, propylene homopolymers, etc.), polyester (e.g., polyethylene terephthalate, polyethylene naphthalate, polybutylene terephthalate, etc.), vinyl chloride polymer, vinyl chloridine polymer, ionomer, etc., as well as combinations thereof. One or multiple panels of the film may be sealed together (e.g., heat sealed), such as at the peripheral edges, to form a cavity within which the device may be stored. For example, a single film may be folded at one or more points and sealed along its periphery to define the cavity within with the device is located. To use the device, the package may be opened, such as by breaking the seal, and the device may then be removed and implanted into a patient.

The present invention may be better understood with reference to the following examples.

Test Methods

Drug Release: The release of a drug compound (e.g., bromelain) may be determined using an in vitro method. More particularly, implantable device samples may be placed in 150 milliliters of an aqueous sodium azide solution. The solutions are enclosed in UV-protected, 250-ml Duran® flasks. The flasks are then placed into a temperature-controlled water bath and continuously shaken at 100 rpm. A temperature of 37° C. is maintained through the release experiments to mimic in vivo conditions. Samples are taken in regular time intervals by completely exchanging the aqueous sodium azide solution. The concentration of the drug compound in solution is determined via UV/Vis absorption spectroscopy using a Cary 1 split beam instrument. From this data, the amount of the drug compound released per sampling interval (microgram per hour) is calculated and plotted over time (hours). Further, the cumulative release ratio of the drug compound is also calculated as a percentage by dividing the amount of the drug compound released at each sampling interval by the total amount of drug compound initially present, and then multiplying this number by 100. This percentage is then plotted over time (hours).

Examples 1-4

Four (4) different types of core layers are formed with varying concentrations of a hydrophobic polymer (Ateva® 4030AC) and a macromolecular biologic (bromelain). To form the samples, bromelain powder is initially melt compounded into Ateva® 4030AC using a Haake Rheomix 600p. First, the Rheomix 600p chamber is filled with Ateva® 4030AC pellets and compounded for 8 minutes at 50° C. The compounding in the Rheomix 600p is done at 50 rpm using roller-type rotors. After 8 minutes, the bromelain powder is added to the Ateva® 4030AC melt and melt mixing continues for 3 minutes at 50° C. After melt mixing, the blend is taken out of the Rheomix 600p and pressed into 1 mm thick sheets using a thermal press. The temperature during pressing is 50° C., the pressing time is 3 minutes, and the pressure is 100 bar. To avoid adhesion of the molten EVA film to the surfaces of the press, a low-adhesion, temperature-tolerant polyester foil (Hostaphan® RNK 23) is placed between the EVA blend and the press plates. After cool down, the polyester films are removed. Discs having a diameter of 25 millimeters are stamped out of the EVA-bromelain sheet using a punching press to create the bromelain containing core layer/monolithic bromelain implants.

The bromelain and Ateva® 4030AC contents inside the different core layers are given in Table 1.

TABLE 1

| Example | Ateva ® 4030AC (wt. %) | Bromelain (wt. %) |
| --- | --- | --- |
| 1 | 80 | 20 |
| 2 | 60 | 40 |
| 3 | 40 | 60 |
| 4 | 20 | 80 |

Figure 5:
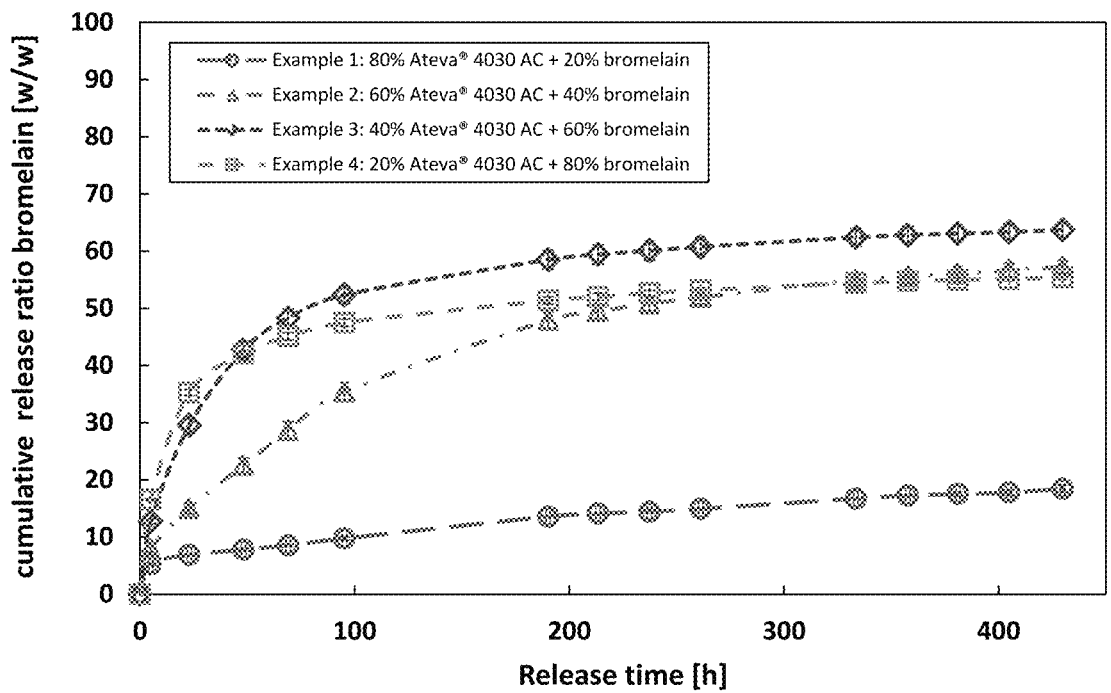
FIG. 5 is a graph showing the cumulative release ratio of bromelain versus release time (hours) for Examples 1-4.
Figure 6:
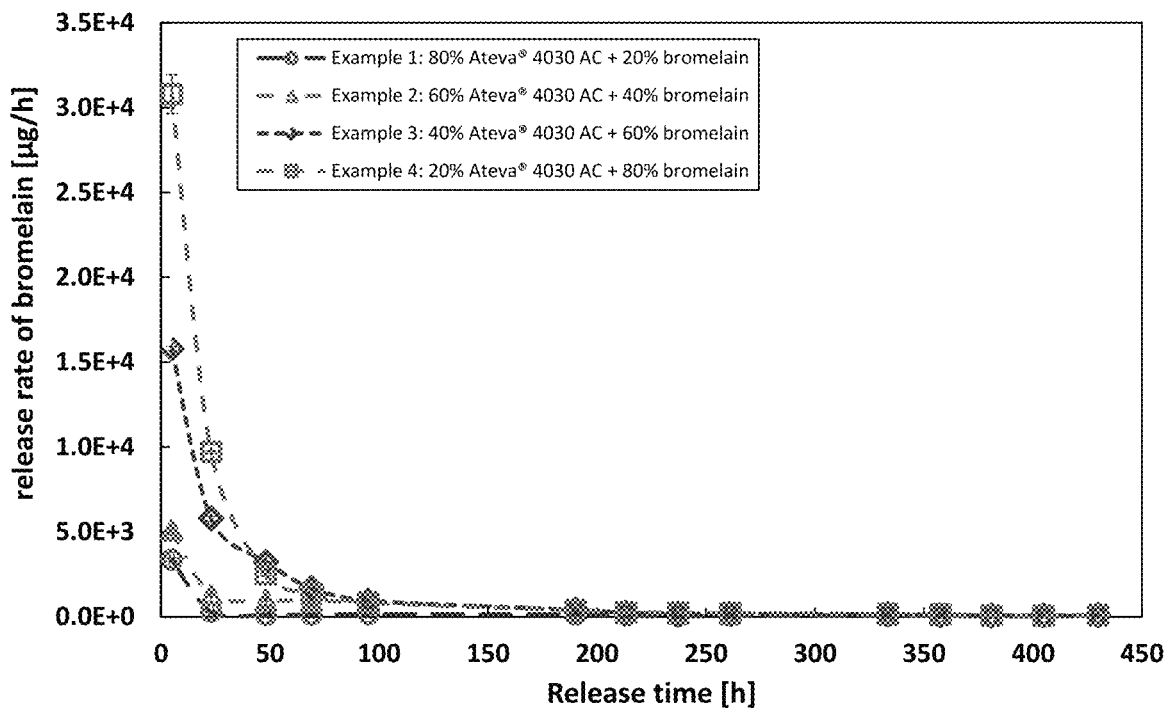
FIG. 6 is a graph showing the release rate of bromelain (µg/h) versus release time (hours) for Examples 1-4.

Once formed, the samples were tested for their release rate as described above. The results are set forth in FIGS. 5-6.

Examples 5-7

Three (3) different types of core-membrane implantable devices are formed using a core layer containing 20 wt. % of a hydrophobic polymer and 80 wt. % of a biologic in combination with varying concentrations of components in the membrane layers. The core layer is formed by melt compounding bromelain powder into Ateva® 4030AC using a Haake Rheomix 600p. First, the Rheomix 600p chamber is filled with Ateva® 4030AC pellets and compounded for 8 minutes at 50° C. The compounding in the Rheomix 600p is done at 50 rpm using roller-type rotors. After 8 minutes, the bromelain powder is added to the Ateva® 4030AC melt and melt mixing continues for 3 minutes at 50° C. After melt mixing, the blend is taken out of the Rheomix 600p and pressed into 1 mm thick sheets using a thermal press. The temperature during pressing is 50° C., the pressing time is 3 minutes, and the pressure is 100 bar. To avoid adhesion of the molten EVA film to the surfaces of the press, a low-adhesion, temperature-tolerant polyester foil (Hostaphan® RNK 23) is placed between the EVA blend and the press plates. After cool down, the polyester films are removed. Discs having a diameter of 23 millimeters are stamped out of the EVA-bromelain sheet using a punching press to create the bromelain containing core layer/monolithic bromelain implants. The membrane layers are formed by melt compounding Ateva® 4030AC and Luviskol® VA64 using a Haake Rheomix 600p in the same manner as described above, except that the resulting discs had a diameter of 25 millimeters. To form the core-membrane implants, a solvent bonding technique is employed. That is, a small amount of toluene is applied on the sides of the discs using a paintbrush and then immediately thereafter the sandwiched layers are bonded and pressed together. Pressure is maintained for a period of 24 hours as the toluene is allowed to evaporate. After this time period, the edge of the core layer is sealed using a highly concentrated toluene solution of Ateva® 4030AC applied from a plastic pipette. The edges are allowed to dry from toluene for a time period of at least 48 hours. Table 2 shows the content of the core and membrane layers used in each Example.

TABLE 2

| | Core Layer (1 mm × 23 mm) | | 2 Membrane Layers (1 mm × 25 mm) | |
| --- | --- | --- | --- | --- |
| Example | Ateva® 4030AC (wt. %) | Bromelain (wt. %) | Ateva® 4030AC (wt. %) | Luviskol® VA64 (wt. %) |
| 5 | 20 | 80 | 80 | 20 |
| 6 | 20 | 80 | 60 | 40 |
| 7 | 20 | 80 | 40 | 60 |

Figure 7:
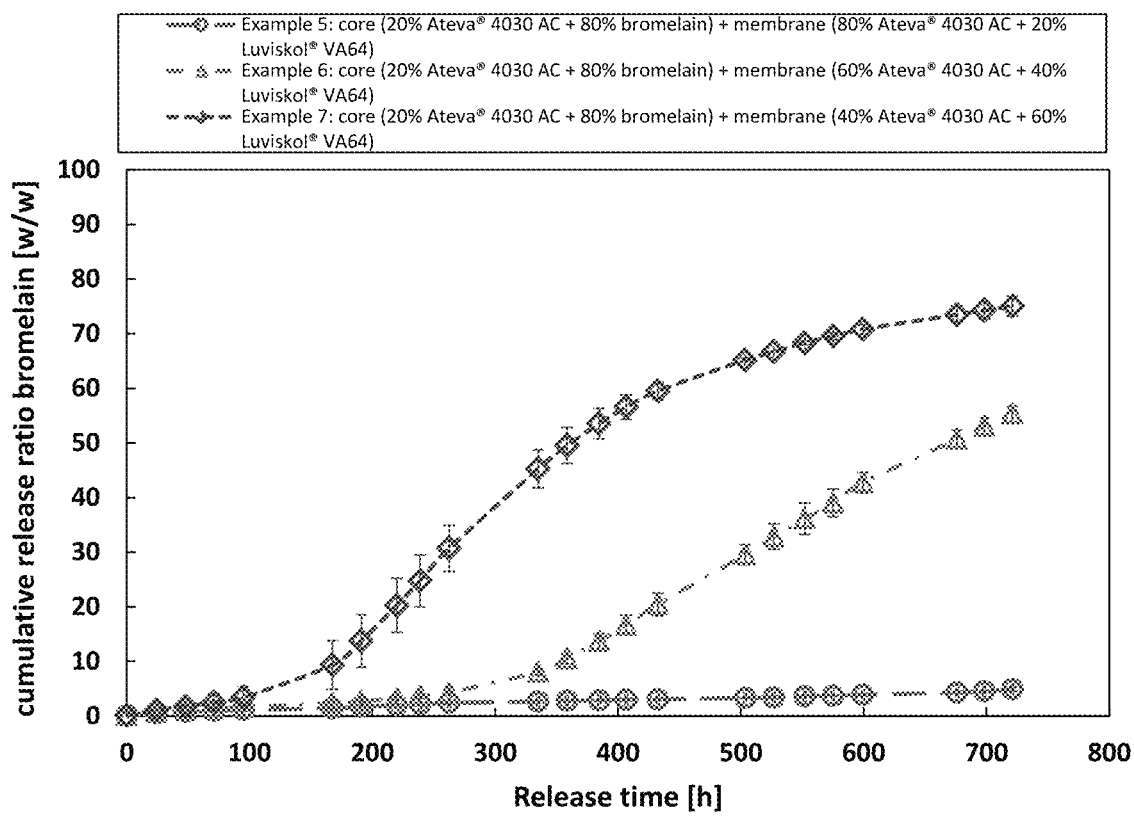
FIG. 7 is a graph showing the cumulative release ratio of bromelain versus release time (hours) for Examples 5-7.
Figure 8:
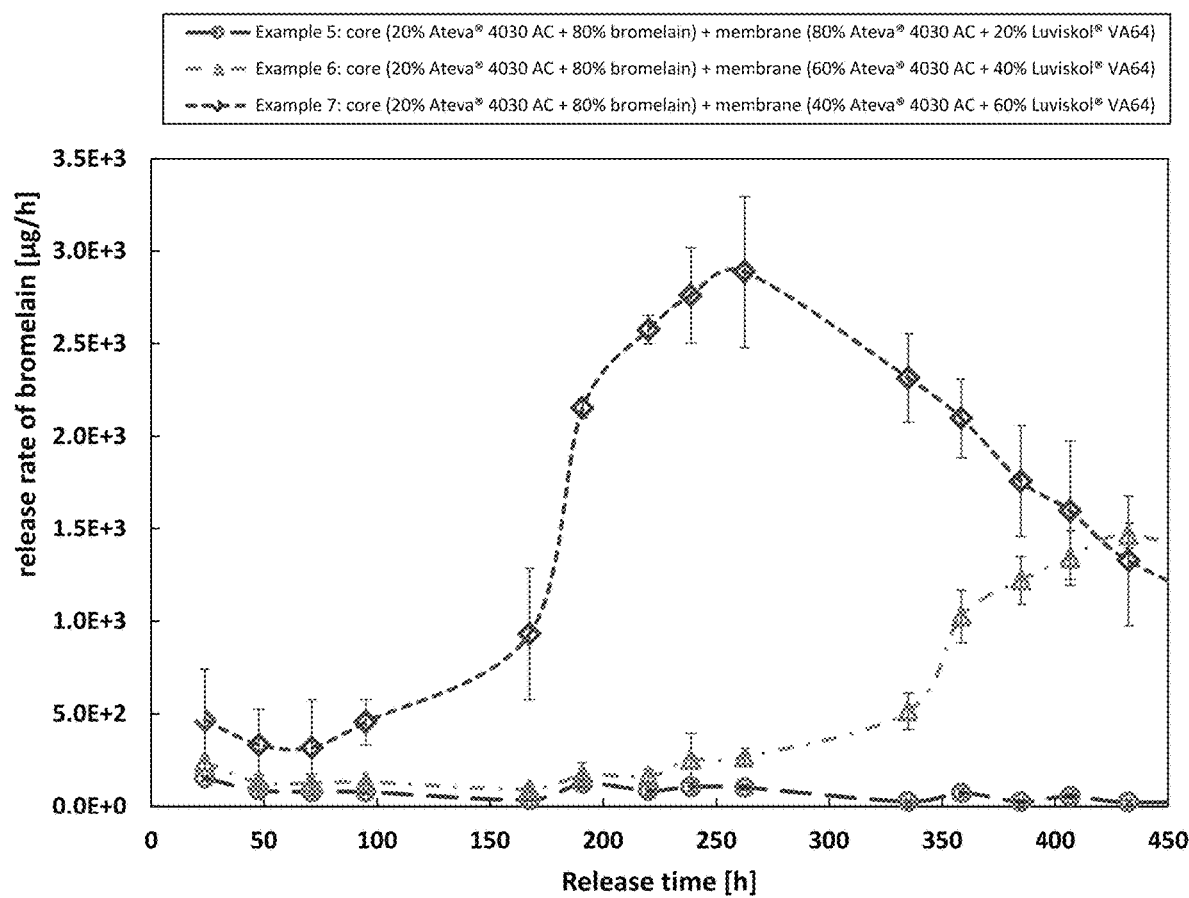
FIG. 8 is a graph showing the release rate of bromelain (µg/h) versus release time (hours) for Examples 5-7.

Once formed, the samples were tested for their release rate as described above. The results are set forth in FIGS. 7-8.

Examples 8-13

Six (6) different types of core-membrane implantable devices are formed using a core layer containing 40 wt. % of a hydrophobic polymer and 60 wt. % of a biologic in combination with varying concentrations of components in the membrane layers. The core layer is formed by melt compounding bromelain powder into Ateva® 4030AC using a Haake Rheomix 600p. First, the Rheomix 600p chamber is filled with Ateva® 4030AC pellets and compounded for 8 minutes at 50° C. The compounding in the Rheomix 600p is done at 50 rpm using roller-type rotors. After 8 minutes, the bromelain powder is added to the Ateva® 4030AC melt and melt mixing continues for 3 minutes at 50° C. After melt mixing, the blend is taken out of the Rheomix 600p and pressed into 1 mm thick sheets using a thermal press. The temperature during pressing is 50° C., the pressing time is 3 minutes, and the pressure is 100 bar. To avoid adhesion of the molten EVA film to the surfaces of the press, a low-adhesion, temperature-tolerant polyester foil (Hostaphan® RNK 23) is placed between the EVA blend and the press plates. After cool down, the polyester films are removed. Discs having a diameter of 23 millimeters are stamped out of the EVA-bromelain sheet using a punching press to create the bromelain containing core layer/monolithic bromelain implants. The membrane layers are formed by melt compounding Ateva® 2861A and polyethylene glycol ("PEG") having a molecular weight of 100,000 grams per mole using a Haake Rheomix 600p in the same manner as described above, except that compounding occurred at a temperature of 170° C. and the resulting discs had a thickness of 0.5 millimeters and a diameter of 25 millimeters. To form the core-membrane implants, a solvent bonding technique is employed. That is, a small amount of toluene is applied on the sides of the discs using a paintbrush and then immediately thereafter the sandwiched layers are bonded and pressed together. Pressure is maintained for a period of 24 hours as the toluene is allowed to evaporate. After this time period, the edge of the core layer is sealed using a highly concentrated toluene solution of Ateva® 4030AC applied from a plastic pipette. The edges are allowed to dry from toluene for a time period of at least 48 hours. Table 3 shows the content of the core and membrane layers used in each Example.

TABLE 3

| | Core Layer (1 mm × 23 mm) | | 2 Membrane Layers (0.5 mm × 25 mm) | |
| --- | --- | --- | --- | --- |
| Example | Ateva® 4030AC (wt. %) | Bromelain (wt. %) | Ateva® 2861A (wt. %) | PEG (wt. %) |
| 8 | 40 | 60 | 99 | 1 |
| 9 | 40 | 60 | 95 | 5 |
| 10 | 40 | 60 | 90 | 10 |
| 11 | 40 | 60 | 75 | 25 |
| 12 | 40 | 60 | 70 | 30 |
| 13 | 40 | 60 | 65 | 35 |

Figure 9:
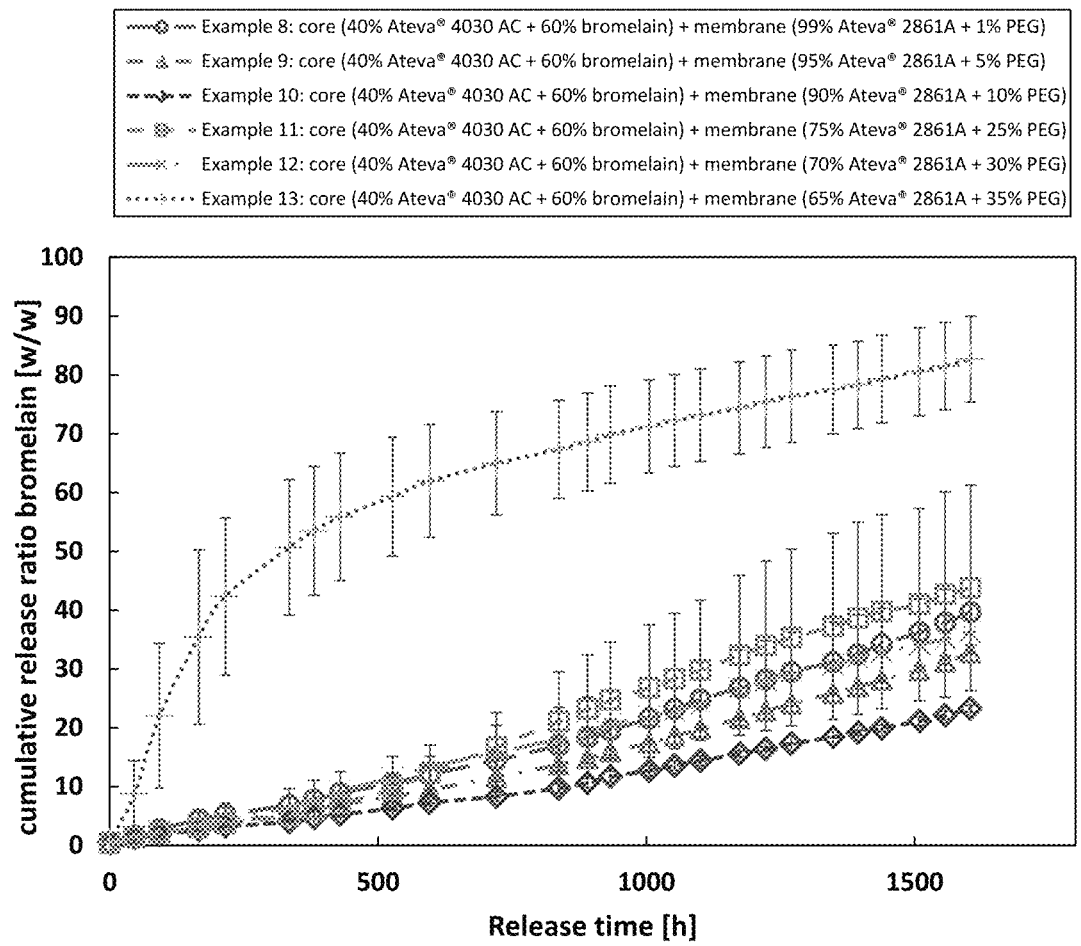
FIG. 9 is a graph showing the cumulative release ratio of bromelain versus release time (hours) for Examples 8-13.
Figure 10:
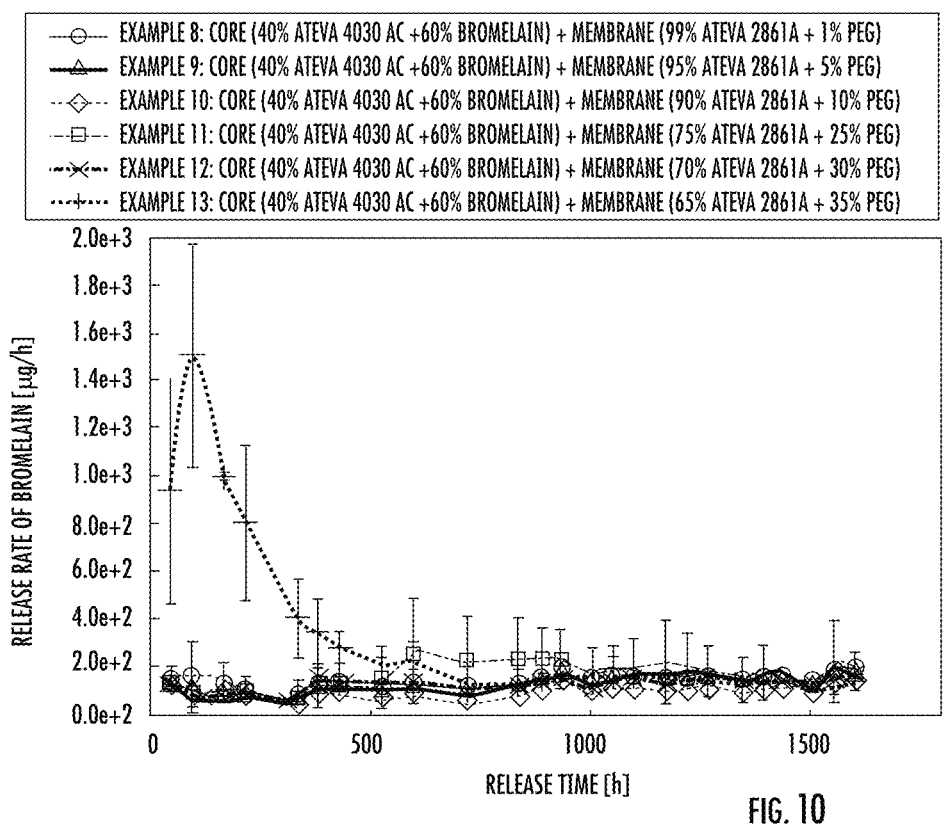
FIG. 10 is a graph showing the release rate of bromelain (µg/h) versus release time (hours) for Examples 8-13.

Once formed, the samples were tested for their release rate as described above. The results are set forth in FIGS. 9-10.

Examples 14-18

Five (5) different types of core-membrane implantable devices are formed using a core layer containing 40 wt. % of a hydrophobic polymer and 60 wt. % of a biologic in combination with varying concentrations of components in the membrane layers. The core layer is formed by melt compounding bromelain powder into Ateva® 4030AC using a Haake Rheomix 600p. First, the Rheomix 600p chamber is filled with Ateva® 4030AC pellets and compounded for 8 minutes at 50° C. The compounding in the Rheomix 600p is done at 50 rpm using roller-type rotors. After 8 minutes, the bromelain powder is added to the Ateva® 4030AC melt and melt mixing continues for 3 minutes at 50° C. After melt mixing, the blend is taken out of the Rheomix 600p and pressed into 1 mm thick sheets using a thermal press. The temperature during pressing is 50° C., the pressing time is 3 minutes, and the pressure is 100 bar. To avoid adhesion of the molten EVA film to the surfaces of the press, a low-adhesion, temperature-tolerant polyester foil (Hostaphan® RNK 23) is placed between the EVA blend and the press plates. After cool down, the polyester films are removed. Discs having a diameter of 23 millimeters are stamped out of the EVA-bromelain sheet using a punching press to create the bromelain containing core layer/monolithic bromelain implants. The membrane layers are formed by melt compounding Ateva® 2861A and Luviskol® VA64 using a Haake Rheomix 600p in the same manner as described above, except that compounding occurred at a temperature of 170° C., the temperature used during pressing was 100° C., and the resulting discs had a thickness of 0.5 millimeters and a diameter of 25 millimeters. To form the core-membrane implants, a solvent bonding technique is employed. That is, a small amount of toluene is applied on the sides of the discs using a paintbrush and then immediately thereafter the sandwiched layers are bonded and pressed together. Pressure is maintained for a period of 24 hours as the toluene is allowed to evaporate. After this time period, the edge of the core layer is sealed using a highly concentrated toluene solution of Ateva® 4030AC applied from a plastic pipette. The edges are allowed to dry from toluene for a time period of at least 48 hours. Table 4 shows the content of the core and membrane layers used in each Example.

TABLE 4

| Example | Core Layer (1 mm × 23 mm) | | 2 Membrane Layers (0.5 mm × 25 mm) | |
|---|---|---|---|---|
| | Ateva® 4030AC (wt. %) | Bromelain (wt. %) | Ateva® 2861A (wt. %) | Luviskol® VA64 (wt. %) |
| 14 | 40 | 60 | 99 | 1 |
| 15 | 40 | 60 | 95 | 5 |
| 16 | 40 | 60 | 90 | 10 |
| 17 | 40 | 60 | 75 | 25 |
| 18 | 40 | 60 | 50 | 50 |

Figure 11:
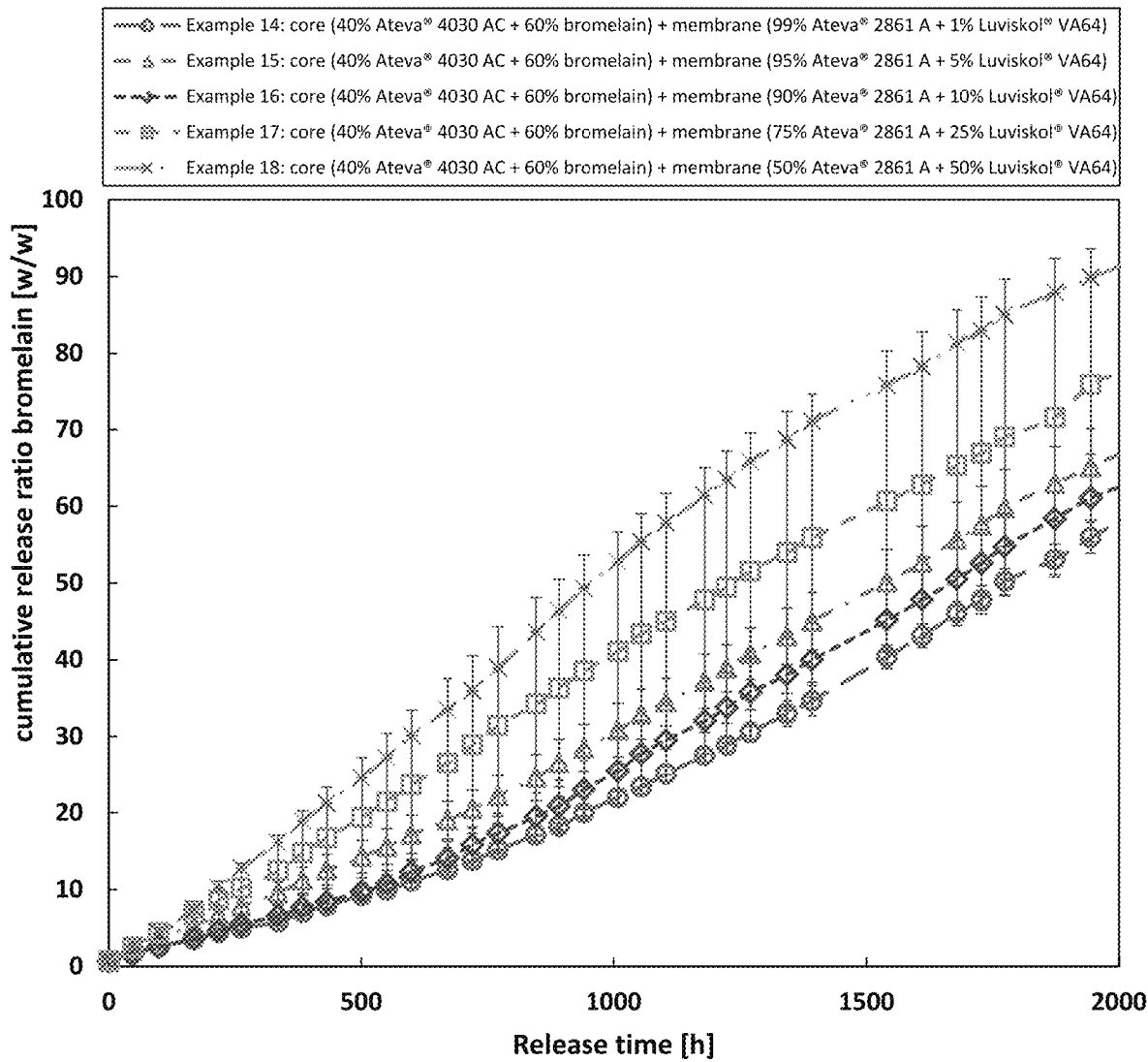
FIG. 11 is a graph showing the cumulative release ratio of bromelain versus release time (hours) for Examples 14-18.
Figure 12:
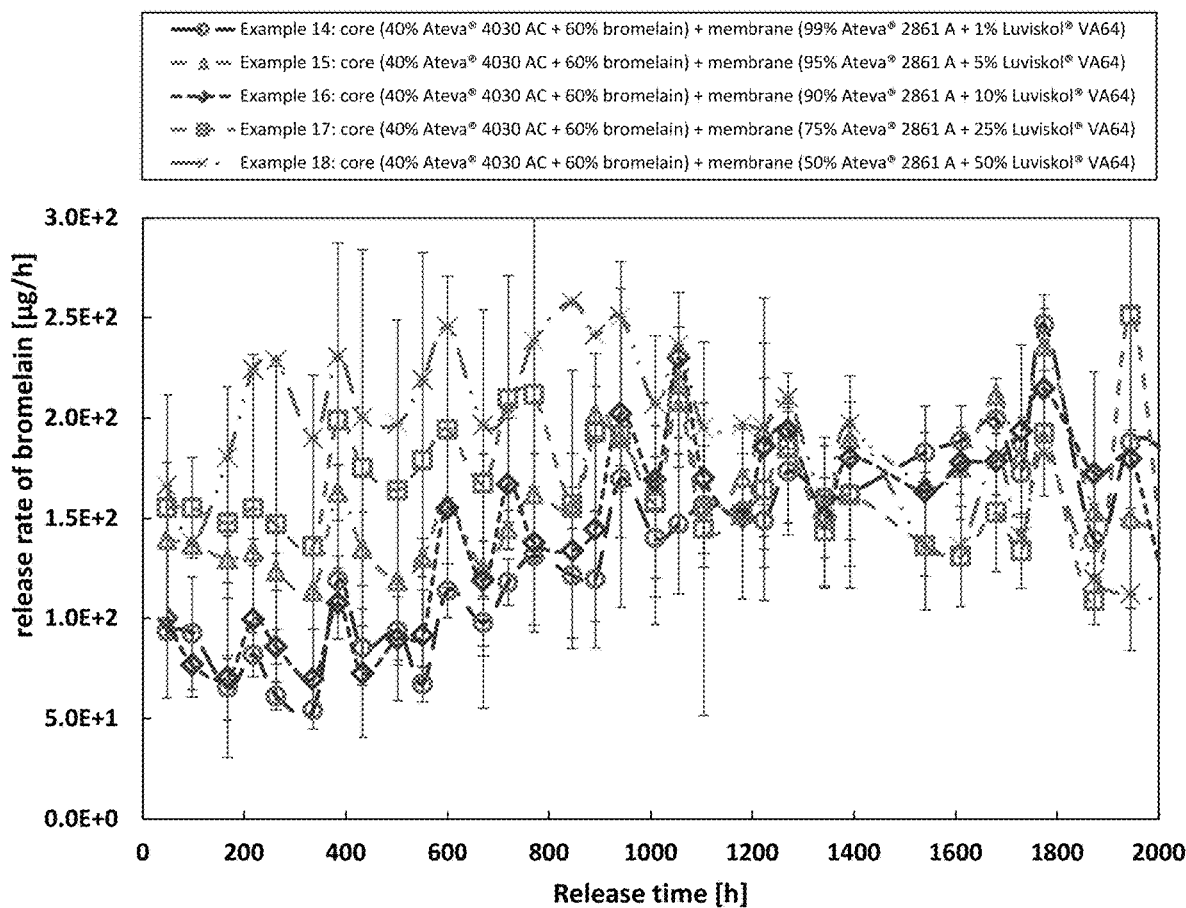
FIG. 12 is a graph showing the release rate of bromelain (µg/h) versus release time (hours) for Examples 14-18.

Once formed, the samples were tested for their release rate as described above. The results are set forth in FIGS. 11-12.

Examples 19-20

Two (2) different types of core-membrane implantable devices are formed using a core layer containing 40 wt. % of a hydrophobic polymer and 60 wt. % of a biologic in combination with varying concentrations of components in the membrane layers. The core layer is formed by melt compounding bromelain powder into Ateva® 4030AC using a Haake Rheomix 600p. First, the Rheomix 600p chamber is filled with Ateva® 4030AC pellets and compounded for 8 minutes at 50° C. The compounding in the Rheomix 600p is done at 50 rpm using roller-type rotors. After 8 minutes, the bromelain powder is added to the Ateva® 4030AC melt and melt mixing continues for 3 minutes at 50° C. After melt mixing, the blend is taken out of the Rheomix 600p and pressed into 1 mm thick sheets using a thermal press. The temperature during pressing is 50° C., the pressing time is 3 minutes, and the pressure is 100 bar. To avoid adhesion of the molten EVA film to the surfaces of the press, a low-adhesion, temperature-tolerant polyester foil (Hostaphan® RNK 23) is placed between the EVA blend and the press plates. After cool down, the polyester films are removed. Discs having a diameter of 23 millimeters are stamped out of the EVA-bromelain sheet using a punching press to create the bromelain containing core layer/monolithic bromelain implants. The membrane layers are formed by melt compounding Ateva® 4030AC, polyethylene glycol ("PEG") having a molecular weight of 100,000 grams per mole, and bromelain powder using a Haake Rheomix 600p in the same manner as described above, except that the resulting discs had a diameter of 25 millimeters. To form the core-membrane implants, a solvent bonding technique is employed. That is, a small amount of toluene is applied on the sides of the discs using a paintbrush and then immediately thereafter the sandwiched layers are bonded and pressed together. Pressure is maintained for a period of 24 hours as the toluene is allowed to evaporate. After this time period, the edge of the core layer is sealed using a highly concentrated toluene solution of Ateva® 4030AC applied from a plastic pipette. The edges are allowed to dry from toluene for a time period of at least 48 hours. Table 5 shows the content of the core and membrane layers used in each Example.

TABLE 5

| Example | Core Layer (1 mm × 23 mm) | | 2 Membrane Layers (1 mm × 25 mm) | | |
|---|---|---|---|---|---|
| | Ateva® 4030AC (wt. %) | Bromelain (wt. %) | Ateva® 4030AC (wt. %) | Bromelain (wt. %) | PEG (wt. %) |
| 19 | 40 | 60 | 75 | 20 | 5 |
| 20 | 40 | 60 | 60 | 20 | 20 |

Figure 13:
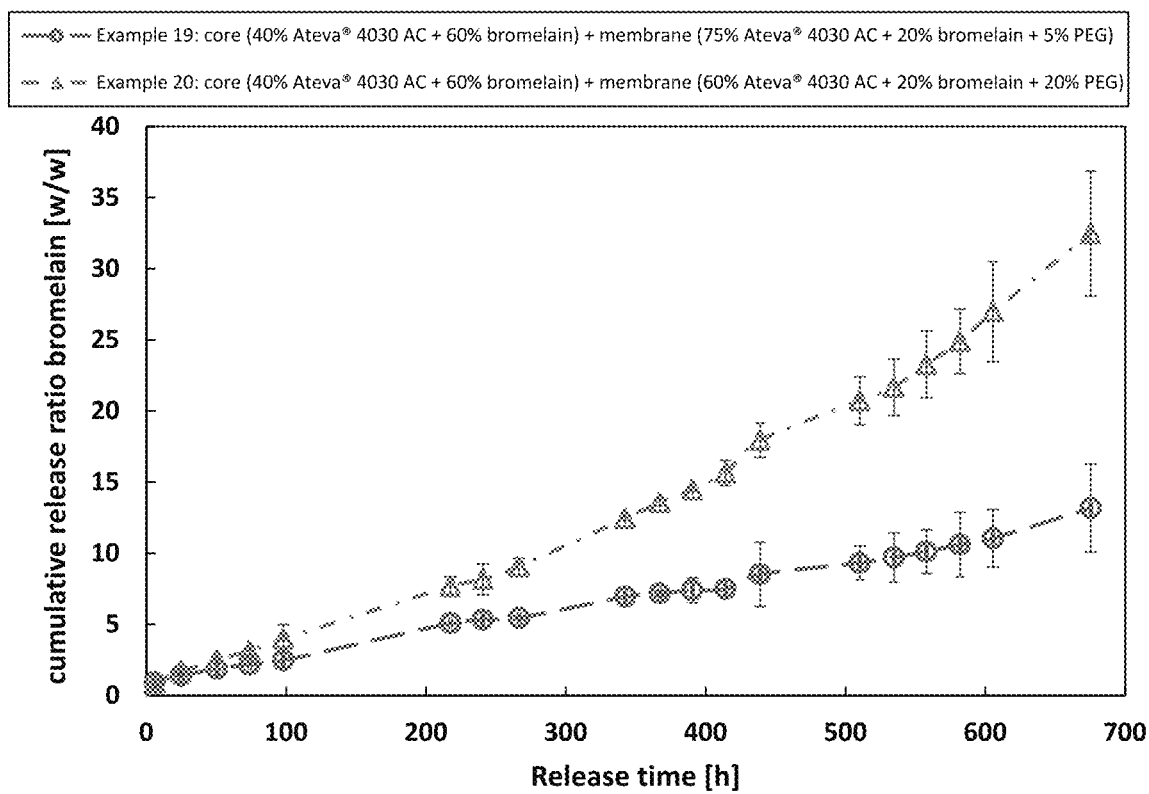
FIG. 13 is a graph showing the cumulative release ratio of bromelain versus release time (hours) for Examples 19-20.
Figure 14:
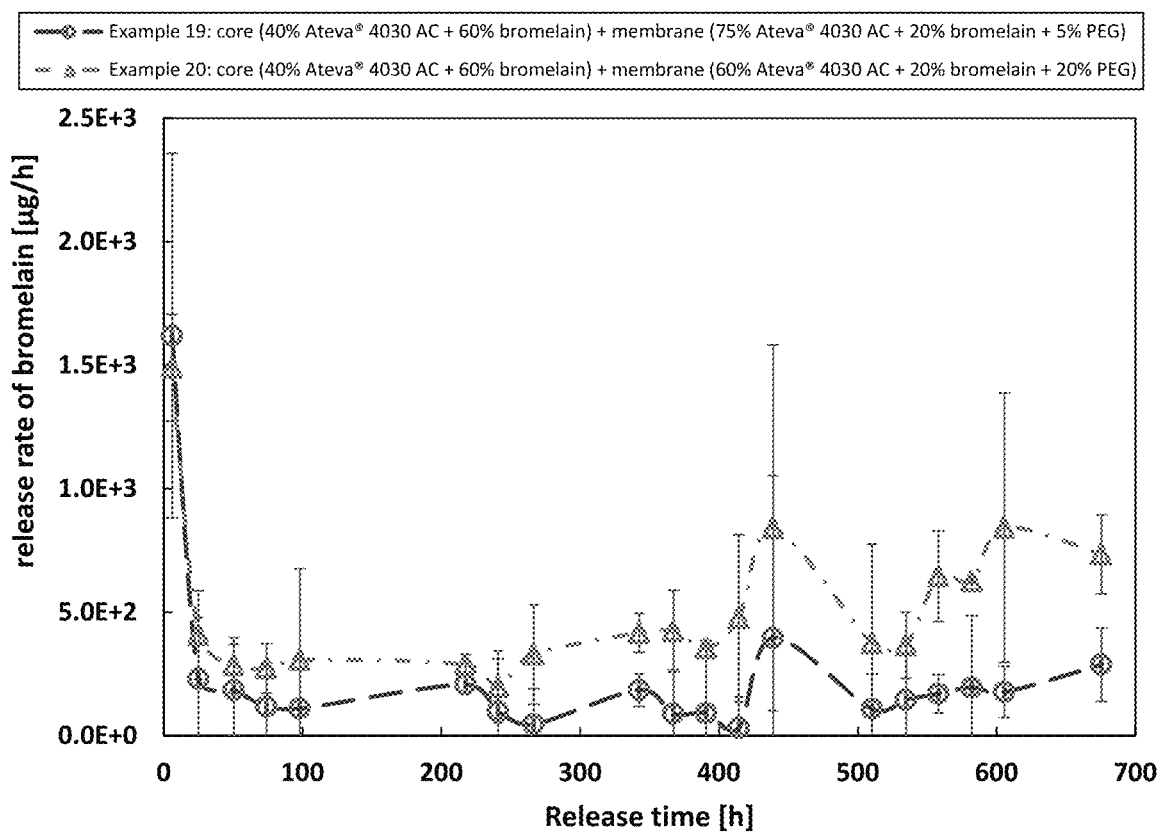
FIG. 14 is a graph showing the release rate of bromelain (µg/h) versus release time (hours) for Examples 19-20.

Once formed, the samples were tested for their release rate as described above. The results are set forth in FIGS. 13-14.

Examples 21-23

Three (3) different types of core-membrane implantable devices are formed using a core layer containing 40 wt. % of a hydrophobic polymer and 60 wt. % of a biologic in combination with varying concentrations of components in the membrane layers. The core layer is formed by melt compounding bromelain powder into Ateva® 4030AC using a Haake Rheomix 600p. First, the Rheomix 600p chamber is filled with Ateva® 4030AC pellets and compounded for 8 minutes at 50° C. The compounding in the Rheomix 600p is done at 50 rpm using roller-type rotors. After 8 minutes, the bromelain powder is added to the Ateva® 4030AC melt and melt mixing continues for 3 minutes at 50° C. After melt mixing, the blend is taken out of the Rheomix 600p and pressed into 1 mm thick sheets using a thermal press. The temperature during pressing is 50° C., the pressing time is 3 minutes, and the pressure is 100 bar. To avoid adhesion of the molten EVA film to the surfaces of the press, a low-adhesion, temperature-tolerant polyester foil (Hostaphan® RNK 23) is placed between the EVA blend and the press plates. After cool down, the polyester films are removed. Discs having a diameter of 23 millimeters are stamped out of the EVA-bromelain sheet using a punching press to create the bromelain containing core layer/monolithic bromelain implants. The membrane layers are formed by melt compounding Ateva® 4030AC and polyethylene glycol ("PEG") having a molecular weight of 100,000 grams per mole using a Haake Rheomix 600p in the same manner as described above, except that compounding occurred at a temperature of 50° C., the temperature used during pressing was 80° C., and the resulting discs had a thickness of 0.5 millimeters and a diameter of 25 millimeters. To form the core-membrane implants, a solvent bonding technique is employed. That is, a small amount of toluene is applied on the sides of the discs using a paintbrush and then immediately thereafter the sandwiched layers are bonded and pressed together. Pressure is maintained for a period of 24 hours as the toluene is allowed to evaporate. After this time period, the edge of the core layer is sealed using a highly concentrated toluene solution of Ateva® 4030AC applied from a plastic pipette. The edges are allowed to dry from toluene for a time period of at least 48 hours.

TABLE 6

| Example | Core Layer (1 mm × 23 mm) | | 2 Membrane Layers (0.5 mm × 25 mm) | |
|---|---|---|---|---|
| | Ateva® 4030AC (wt. %) | Bromelain (wt. %) | Ateva® 4030AC (wt. %) | PEG (wt. %) |
| 21 | 40 | 60 | 95 | 5 |
| 22 | 40 | 60 | 80 | 20 |
| 23 | 40 | 60 | 70 | 30 |

Figure 15:
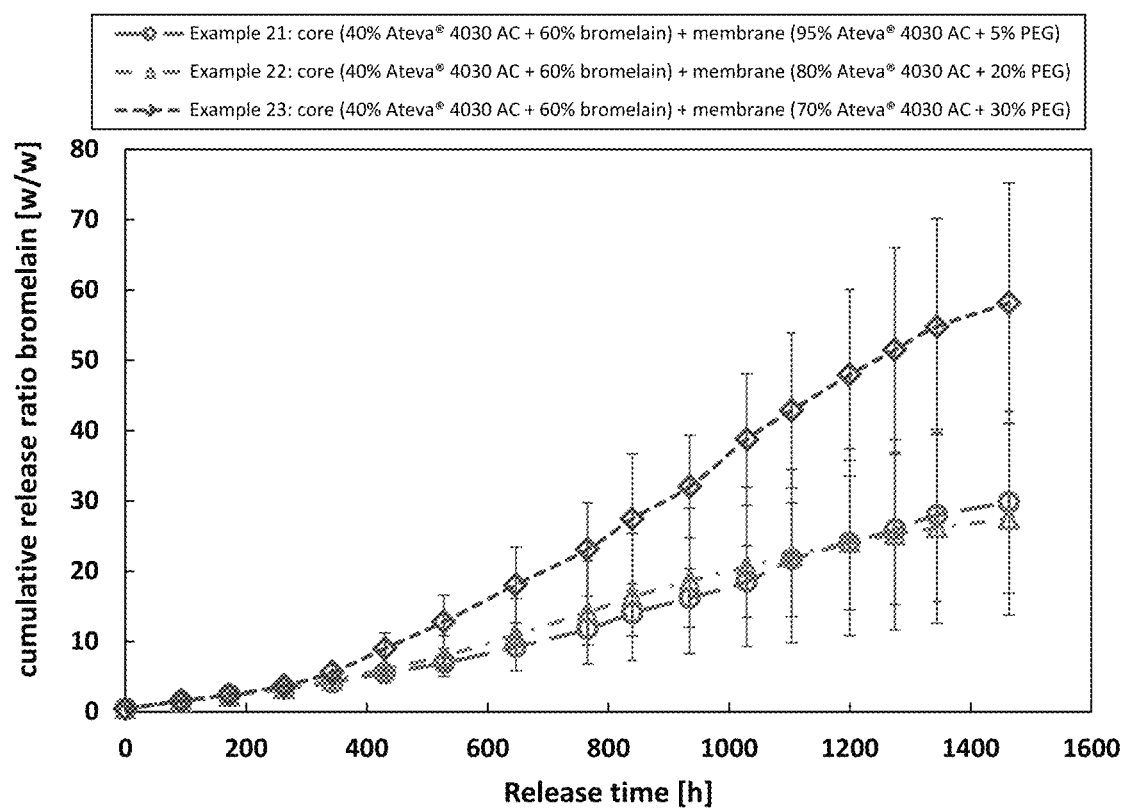
FIG. 15 is a graph showing the cumulative release ratio of bromelain versus release time (hours) for Examples 21-23.
Figure 16:
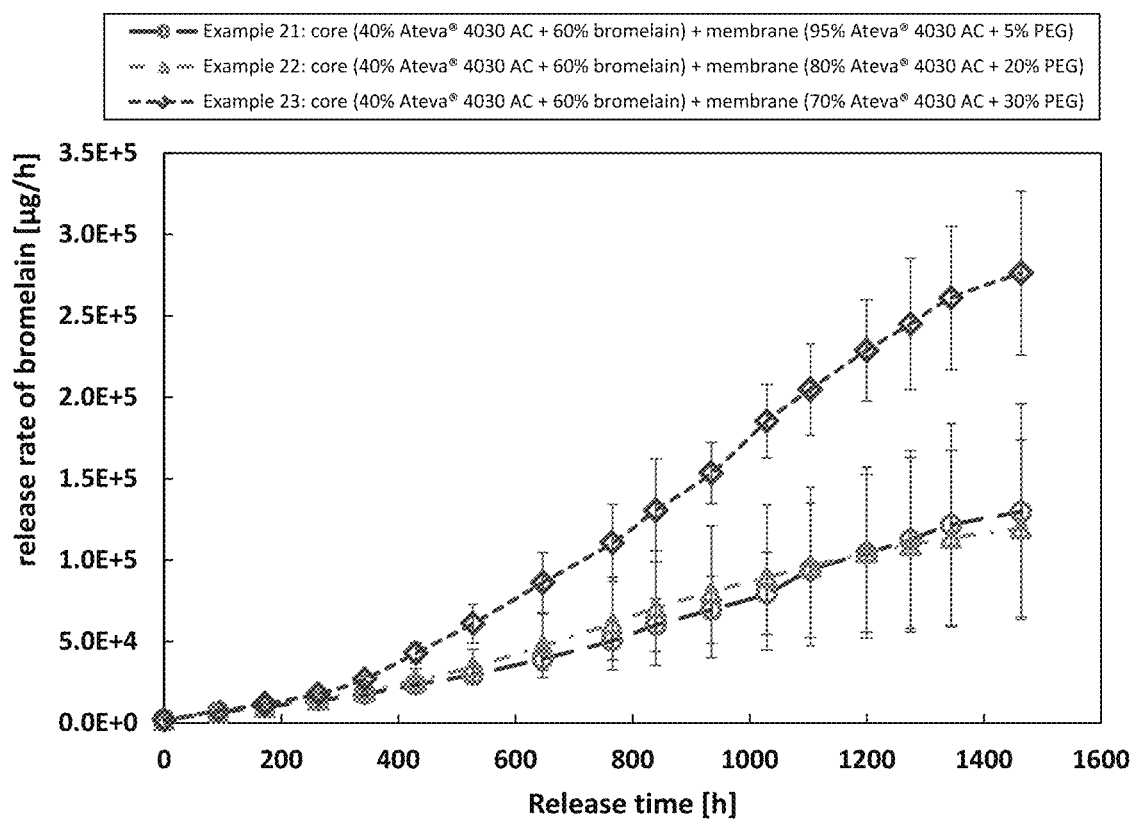
FIG. 16 is a graph showing the release rate of bromelain (µg/h) versus release time (hours) for Examples 21-23.

Once formed, the samples were tested for their release rate as described above. The results are set forth in FIGS. 15-16.

Examples 24-27

Four (4) different types of core-membrane implantable devices are formed using a core layer containing 40 wt. % of a hydrophobic polymer and 60 wt. % of a biologic in combination with varying concentrations of components in the membrane layers. The core layer is formed by melt compounding collagen powder into Ateva® 4030AC using a Haake Rheomix 600p. First, the Rheomix 600p chamber is filled with Ateva® 4030AC pellets and compounded for 8 minutes at 50° C. The compounding in the Rheomix 600p is done at 50 rpm using roller-type rotors. After 8 minutes, the collagen powder is added to the Ateva® 4030AC melt and melt mixing continues for 3 minutes at 50° C. After melt mixing, the blend is taken out of the Rheomix 600p and pressed into 1 mm thick sheets using a thermal press. The temperature during pressing is 50° C., the pressing time is 3 minutes, and the pressure is 100 bar. To avoid adhesion of the molten EVA film to the surfaces of the press, a low-adhesion, temperature-tolerant polyester foil (Hostaphan® RNK 23) is placed between the EVA blend and the press plates. After cool down, the polyester films are removed. Discs having a diameter of 23 millimeters are stamped out of the EVA-collagen sheet using a punching press to create the collagen containing core layer/monolithic collagen implants. The membrane layers are formed by melt compounding Ateva® 4030AC and Luviskol® VA64 using a Haake Rheomix 600p in the same manner as described above, except that compounding occurred at a temperature of 50° C., the temperature used during pressing was 50° C., and the resulting discs had a thickness of 1.0 millimeters and a diameter of 25 millimeters. To form the core-membrane implants, a solvent bonding technique is employed. That is, a small amount of toluene is applied on the sides of the discs using a paintbrush and then immediately thereafter the sandwiched layers are bonded and pressed together. Pressure is maintained for a period of 24 hours as the toluene is allowed to evaporate. After this time period, the edge of the core layer is sealed using a highly concentrated toluene solution of Ateva® 4030AC applied from a plastic pipette. The edges are allowed to dry from toluene for a time period of at least 48 hours. Table 7 shows the content of the core and membrane layers used in each Example.

TABLE 7

| Example | Core Layer (1 mm × 23 mm) | | 2 Membrane Layers (1 mm × 25 mm) | |
|---|---|---|---|---|
| | Ateva® 4030AC (wt. %) | Collagen (wt. %) | Ateva® 4030AC (wt. %) | Luviskol® VA64 (wt. %) |
| 24 | 40 | 60 | 75 | 25 |
| 25 | 40 | 60 | 70 | 30 |
| 26 | 40 | 60 | 65 | 35 |
| 27 | 40 | 60 | 60 | 40 |

Figure 17:
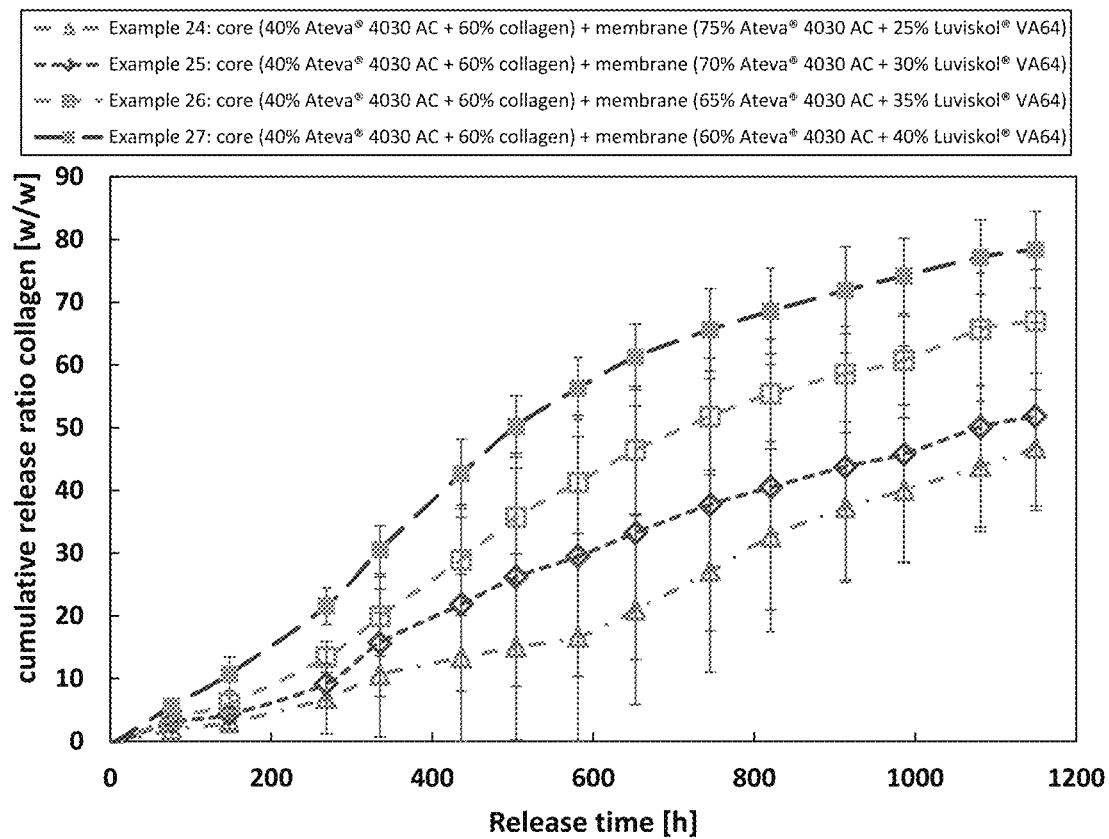
FIG. 17 is a graph showing the cumulative release ratio of collagen versus release time (hours) for Examples 24-27.
Figure 18:
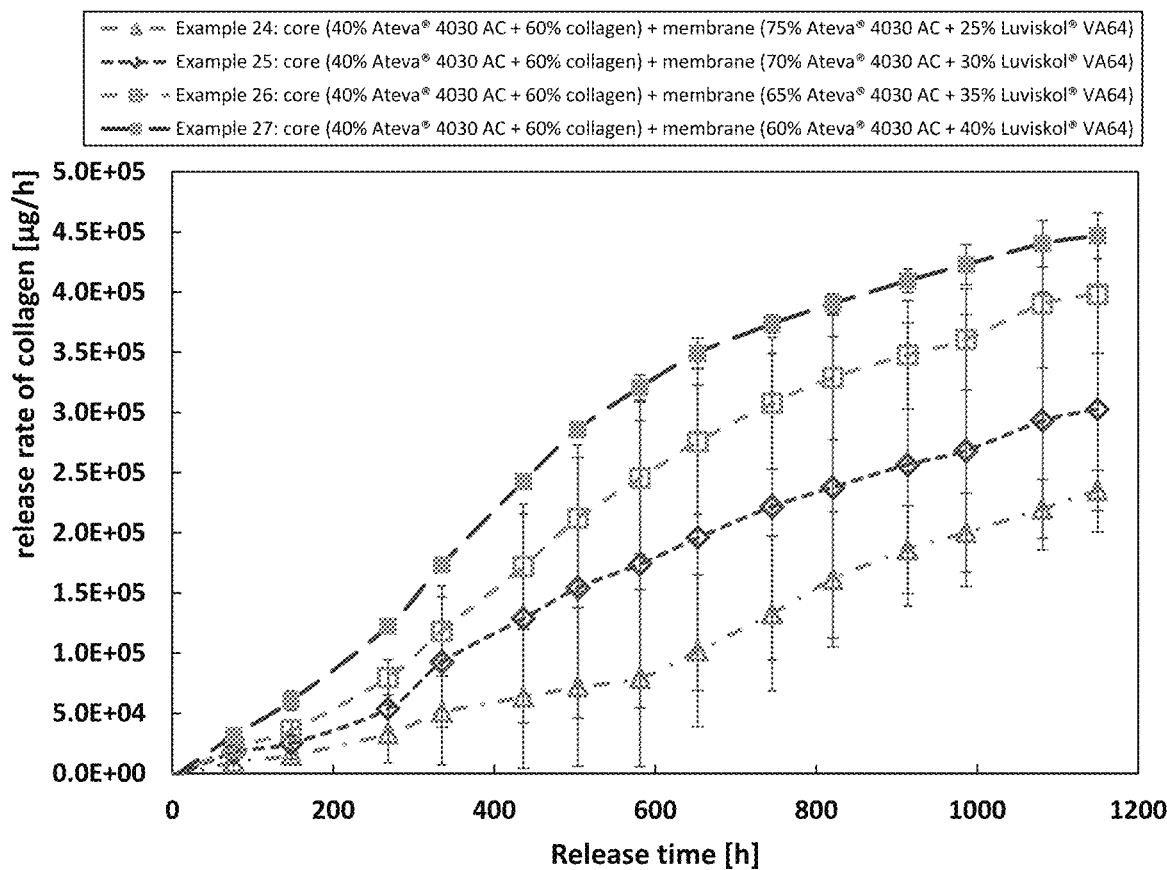
FIG. 18 is a graph showing the release rate of collagen (µg/h) versus release time (hours) for Examples 24-27.

Once formed, the samples were tested or their release rate as described above. The results are set forth in FIGS. 17-18.

Examples 28-30

Three (3) different types of core-membrane implantable devices are formed using a core layer containing 40 wt. % of a hydrophobic polymer and 60 wt. % of a biologic in combination with varying with varying concentrations of components in the membrane layers. The core rod is formed by melt compounding bromelain powder into Ateva® 4030AC using a DSM bench top double-screw extruder with conical, intermeshing screws. First, Ateva® 4030AC (1 mm fine powder) is dry blended with bromelain. The blended mixture is then fed into the DSM extruder. The extrusion temperature was 60° C. and the screw speed was 50 rpm. The extruded filament is allowed to cool down to room temperature and then cut into 30 mm long rods. The diameter of the extruded filament was 3.4 mm. The membrane layer is formed by melt compounding Luviskol® VA64 powder into Ateva® 4030AC using a Haake Rheomix 600p. First, the Rheomix 600p chamber is filled with Ateva® 4030AC pellets and compounded for 8 minutes at 50° C. The compounding in the Rheomix 600p is done at 50 rpm using roller-type rotors. After 8 minutes, the Luviskol® VA64 powder is added to the Ateva® 4030AC melt and melt mixing continues for 3 minutes at 50° C. After melt mixing, the blend is taken out of the Rheomix 600p and pressed into 1 mm thick sheets using a thermal press. The temperature during pressing is 50° C., the pressing time is 3 minutes, and the pressure is 100 bar.

To avoid adhesion of the molten Ateva® 4030AC film to the surfaces of the press, a low-adhesion, temperature-tolerant polyester foil (Hostaphan® RNK 23) is placed between the Ateva® 4030AC blend and the press plates. After cool down, the polyester films are removed. To form the core-membrane implants, a temperature bonding technique is employed. That is the membrane layers and the core rods are heated to 55° C. for 30 minutes. A single membrane layer is then attached to a single core rod manually by applying gentle pressure while rolling the specimen for a prolonged period of time. After this, both ends of the cylinders and the seam between the ends of the membrane layer are sealed using a highly concentrated toluene solution of Ateva® 4030AC applied from a plastic pipette. The edges and the seam are allowed to dry from toluene for a time period of at least 48 hours. Table 8 shows the content of the core and membrane layers used in each Example.

TABLE 8

| | Core Rod (diameter 3.4 mm; length 30 mm) | | Membrane Layer (thickness: 1 mm) | |
|---|---|---|---|---|
| Example | Ateva® 4030AC (wt. %) | Bromelain (wt. %) | Ateva® 4030AC (wt. %) | Luviskol® VA64 (wt. %) |
| 28 | 40 | 60 | 80 | 20 |
| 29 | 40 | 60 | 70 | 30 |
| 30 | 40 | 60 | 60 | 40 |

Figure 19:
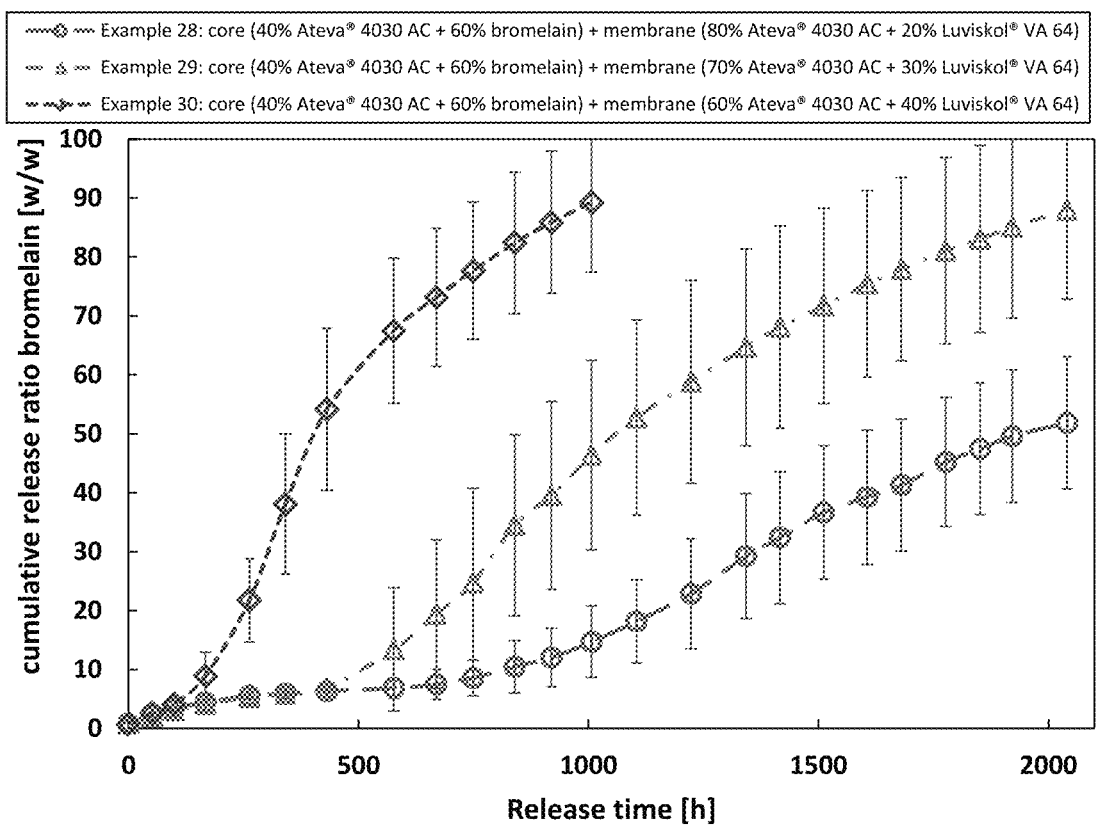
FIG. 19 is a graph showing the cumulative release ratio of bromelain versus release time (hours) for Examples 28-30.
Figure 20:
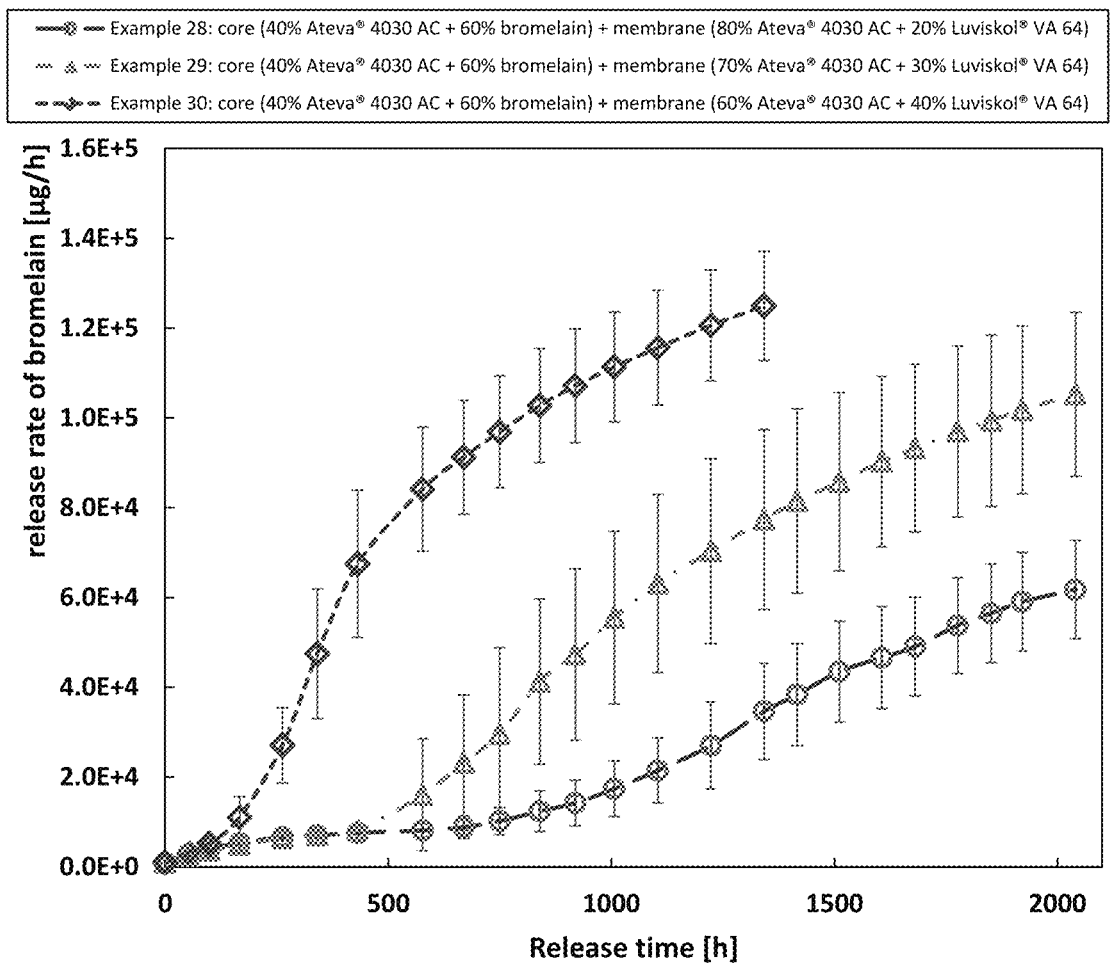
FIG. 20 is a graph showing the release rate of bromelain (µg/h) versus release time (hours) for Examples 28-30.

Once formed, the samples were tested for their release rate as described above. The results are set forth in FIGS. 19-20.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An implantable device for delivery of a macromolecular drug compound, the device comprising:
   a core having an outer surface, wherein the core comprises a core polymer matrix within which is dispersed a drug compound having a molecular weight of about 0.5 kDa or more, the polymer matrix containing a first ethylene vinyl acetate copolymer; and
   a membrane layer positioned adjacent to the outer surface of the core, wherein the membrane layer comprises a membrane polymer matrix within which the macromolecular drug compound is optionally dispersed, wherein the membrane polymer matrix contains a second ethylene vinyl acetate copolymer in combination with a hydrophilic compound, wherein the weight ratio of the second ethylene vinyl acetate copolymer to the hydrophilic compound within the membrane polymer matrix ranges from at least about 2.3 to about 99.

2. The implantable device of claim 1, wherein the device has a generally circular cross-sectional shape.

3. The implantable device of claim 2, wherein the device has a diameter of from about 0.5 to about 50 millimeters.

4. The implantable device of claim 2, wherein the device is in the form of a cylinder.

5. The implantable device of claim 1, wherein the device is in the form of a disc.

6. The implantable device of claim 1, wherein macromolecular drug compounds constitute from about 5 wt. % to about 60 wt. % of the core and the core polymer matrix constitutes from about 40 wt. % to about 95 wt. % of the core.

7. The implantable device of claim 1, wherein after a time period of 30 days, the device exhibits a cumulative release ratio of the macromolecular drug compound of from about 40% to about 85%.

8. The implantable device of claim 1, wherein the first ethylene vinyl acetate copolymer or the second vinyl acetate copolymer has a vinyl acetate content of from about 10 wt. % to about 45 wt. % of the copolymer.

9. The implantable device of claim 1, wherein the first ethylene vinyl acetate copolymer has a melting temperature of from about 40° C. to about 140° C. as determined in accordance with ASTM D3418-15.

10. The implantable device of claim 1, wherein the first ethylene vinyl acetate copolymer or the second ethylene vinyl acetate copolymer, or both has a melt flow index of from about 0.2 to about 100 grams per 10 minutes as determined in accordance with ASTM D1238-13 at a temperature of 190° C. and a load of 2.16 kilograms.

11. The implantable device of claim 1, wherein the macromolecular drug compound is a protein, peptide, enzyme, antibody, interferon, interleukin, blood factor, vaccine, nucleotide, lipid, or a combination thereof.

12. The implantable device of claim 1, wherein the membrane polymer matrix constitutes from about 30 wt. % to 99 wt. % of the membrane layer.

13. The implantable device of claim 1, wherein the membrane layer is free of the macromolecular drug compound.

14. The implantable device of claim 1, wherein the macromolecular drug compound constitutes from about 1 wt. % to about 40 wt. % of the membrane layer.

15. The implantable device of claim 14, wherein the ratio of the concentration of the macromolecular drug compound in the core to the concentration of the macromolecular drug compound in the membrane layer is about 1.5 or more.

16. The implantable device of claim 1, wherein the ratio of the melt flow index of the first ethylene vinyl acetate copolymer to the melt flow index of the second ethylene vinyl acetate copolymer is from about 1 to about 20, as determined in accordance with ASTM D1238-13 at a temperature of 190° C. and a load of 2.16 kilograms.

17. The implantable device of claim 1, wherein the hydrophilic compound is a hydrophilic polymer.

18. The implantable device of claim 17, wherein the hydrophilic polymer includes a sodium, potassium or calcium alginate, carboxymethylcellulose, agar, gelatin, polyvinyl alcohol, polyalkylene glycol, collagen, pectin, chitin, chitosan, poly-1-caprolactone, polyvinylpyrrolidone, poly(vinylpyrrolidone-co-vinyl acetate), polysaccharide, hydrophilic polyurethane, polyhydroxyacrylate, dextran, xanthan, hydroxypropyl cellulose, methylcellulose, protein, ethylene vinyl alcohol copolymer, water-soluble polysilane, water-soluble silicone, water-soluble polyurethane, or a combination thereof.

19. The implantable device of claim 1, wherein the core, membrane layer, or both contain a radiocontrast agent.

20. The implantable device of claim 1, further comprising a second membrane layer positioned adjacent to an outer surface of the membrane layer.

21. A method for prohibiting and/or treating a condition, disease, and/or cosmetic state of a patient, the method comprising subcutaneously implanting the device of claim 1 in the patient.

* * * * *

UNITED STATES PATENT AND TRADEMARK OFFICE
CERTIFICATE OF CORRECTION

PATENT NO. : 12,108,225 B2
APPLICATION NO. : 18/315618
DATED : October 1, 2024
INVENTOR(S) : Christian Schneider Page 1 of 1

It is certified that error appears in the above-identified patent and that said Letters Patent is hereby corrected as shown below:

On the Title Page

Under item (60), Related U.S. Application Data:
"(60) Provisional application No 62/675,995, filed on May 24, 2018." should read --(60) Provisional application No 62/675,994, filed on May 24, 2018.--

Signed and Sealed this
Twenty-first Day of January, 2025

Coke Morgan Stewart
*Acting Director of the United States Patent and Trademark Office*